US009745530B2

(12) United States Patent
Ruan et al.

(10) Patent No.: US 9,745,530 B2
(45) Date of Patent: Aug. 29, 2017

(54) PRODUCTION OF BIODIESEL FROM SCUM

(71) Applicants: Rongsheng Ruan, Arden Hills, MN (US); Min Min Addy, Falcon Heights, MN (US); Yong Nie, Beijing (CN); Erik Andrew Anderson, Minneapolis, MN (US); Chonghao Bi, Beijing (CN); Dong Li, Beijing (CN); Ling Chen, Roseville, MN (US)

(72) Inventors: Rongsheng Ruan, Arden Hills, MN (US); Min Min Addy, Falcon Heights, MN (US); Yong Nie, Beijing (CN); Erik Andrew Anderson, Minneapolis, MN (US); Chonghao Bi, Beijing (CN); Dong Li, Beijing (CN); Ling Chen, Roseville, MN (US)

(73) Assignees: Regents of the University of Minnesota, Minneapolis, MN (US); China Agricultural University, Beijing (CN)

( * ) Notice: Subject to any disclaimer, the term of this patent is extended or adjusted under 35 U.S.C. 154(b) by 0 days.

(21) Appl. No.: 15/019,707

(22) Filed: Feb. 9, 2016

(65) Prior Publication Data

US 2016/0230106 A1    Aug. 11, 2016

Related U.S. Application Data

(60) Provisional application No. 62/113,853, filed on Feb. 9, 2015.

(51) Int. Cl.
*C10L 1/08*    (2006.01)
*C11B 13/00*    (2006.01)
(Continued)

(52) U.S. Cl.
CPC ............... *C10L 1/08* (2013.01); *C07C 67/02* (2013.01); *C11B 3/04* (2013.01); *C11B 13/00* (2013.01);
(Continued)

(58) Field of Classification Search
CPC . C11B 13/00; C11B 3/04; C07C 67/02; C10L 2200/0476; C10L 2200/0484; C10L 2290/543; C10L 2290/545
See application file for complete search history.

(56) References Cited

U.S. PATENT DOCUMENTS

2014/0194634 A1*    7/2014    Lu ........................... C10L 1/026
554/157

FOREIGN PATENT DOCUMENTS

CN    103497842    *    1/2014    ............... C11C 3/10

OTHER PUBLICATIONS

CN 103497842, Wang, Q, et al., Method for preparing biodiesel fuel from waste cooking oil using methanol and ethanol as transesterification agents, 2014, 1 page abstract.*

* cited by examiner

*Primary Examiner* — Yate K Cutliff
(74) *Attorney, Agent, or Firm* — Schwegman Lundberg & Woessner, P.A.

(57) ABSTRACT

A method for production of a biodiesel is described herein. The method for production of a biodiesel comprises (a) separating solids from a waste oil composition to provide a clarified oil composition; (b) acidifying the clarified oil composition to produce an acidified oil composition including free fatty acids derived from the waste oil; (c) converting at least a portion of the free fatty acids in the acidified oil composition to glycerides to provide a glyceride composition; and (d) reacting at least a portion of the glycerides in
(Continued)

the glyceride composition with methanol to form fatty acid methyl ester to provide a biodiesel composition.

20 Claims, 8 Drawing Sheets

(51) Int. Cl.
*C11B 3/04* (2006.01)
*C07C 67/02* (2006.01)
*C11C 3/02* (2006.01)
*C11C 3/06* (2006.01)
*C11C 3/00* (2006.01)

(52) U.S. Cl.
CPC *C11C 3/02* (2013.01); *C11C 3/06* (2013.01); *C10L 2200/0476* (2013.01); *C10L 2270/026* (2013.01); *C10L 2290/06* (2013.01); *C10L 2290/08* (2013.01); *C10L 2290/543* (2013.01); *C10L 2290/545* (2013.01); *C11C 3/003* (2013.01); *Y02E 50/13* (2013.01); *Y02W 30/74* (2015.05)

PRODUCTION OF BIODIESEL FROM SCUM

CROSS-REFERENCE TO RELATED APPLICATIONS

This application claims priority to U.S. Provisional Patent Application 62/113,853 filed on Feb. 9, 2015, which application is incorporated by reference herein in its entirety.

BACKGROUND

As a renewable fuel, biodiesel has become an attractive alternative for a diesel fuel substitute. Since the 1990s, vegetable oil has been the major source for global biodiesel production. Biodiesel-alternative fuel makes inroads but hurdles remain. For example, soybean oil was the largest biodiesel feedstock in the U.S. for the past several years. However, despite the wide use of vegetable oil as a feedstock for the production of vegetable oil, its high cost has limited the viability of biodiesel as a competitive fuel. For vegetable-oil based biodiesel, the feedstock alone amounts to about 70-80% of the total production cost.

BRIEF DESCRIPTION OF THE FIGURES

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
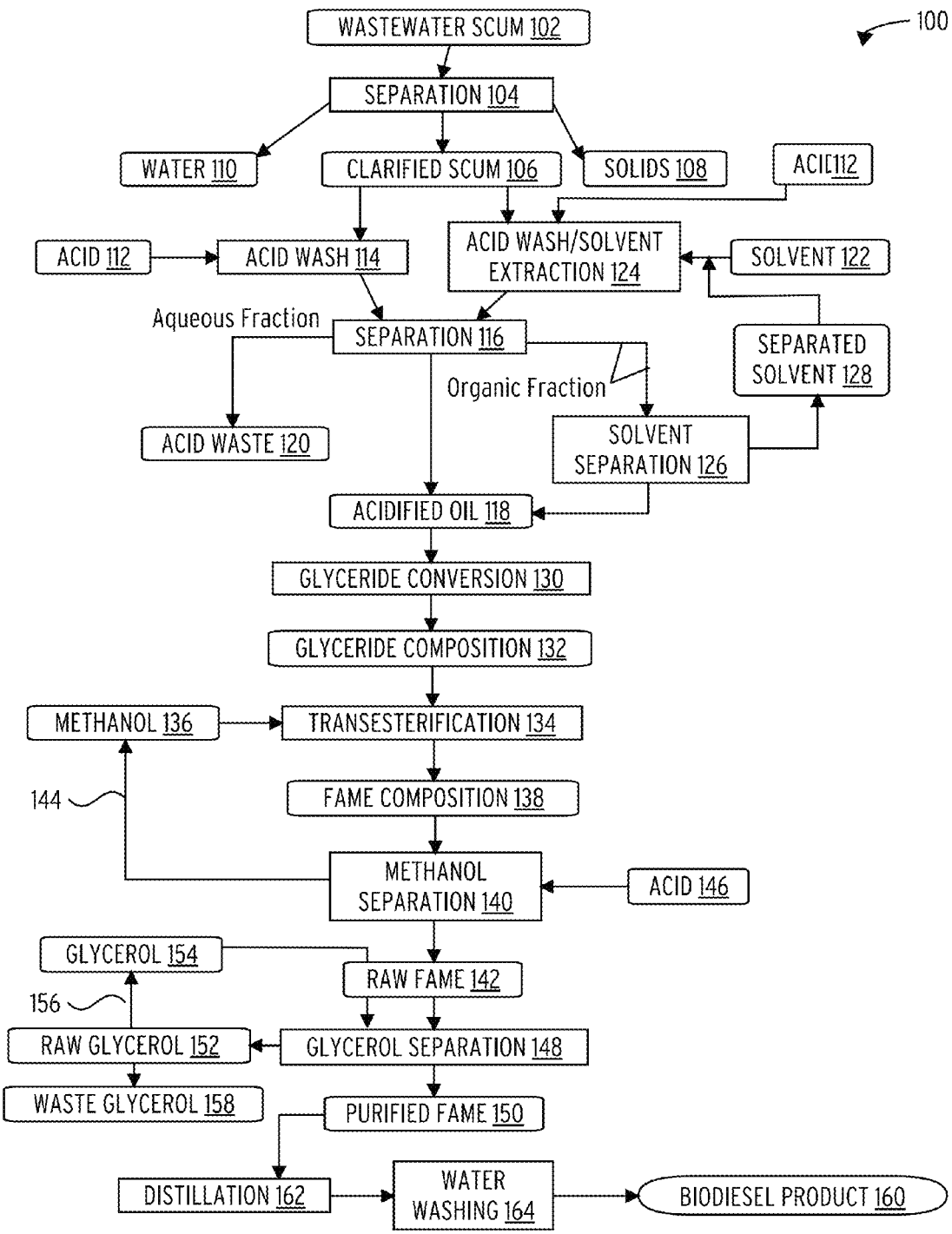
FIG. 1 is a flow diagram of an example process for converting scum to biodiesel.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Definitions

Values expressed in orange format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1 to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. A comma can be used as a delimiter or digit group separator to the left or right of a decimal mark; for example, "0.000,1" is equivalent to "0.0001." All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "organic group" as used herein refers to but is not limited to any carbon-containing functional group. For example, an oxygen-containing group such as an alkoxy group, aryloxy group, aralkyloxy group, oxo carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, $SO_2R$, $SO_2N(R)_2$, $SO_3R$, $C(O)R$, $C(O)C(O)R$, $C(O)CH_2C(O)R$, $C(S)R$, $C(O)OR$, $OC(O)R$, $C(O)N(R)_2$, $OC(O)N(R)_2$, $C(S)N(R)_2$, $(CH_2)_{0-2}N(R)C(O)R$, $(CH_2)_{0-2}N(R)N(R)_2$, $N(R)N(R)C(O)R$, $N(R)N(R)C(O)OR$, $N(R)N(R)CON(R)_2$, $N(R)SO_2R$, $N(R)SO_2N(R)_2$, $N(R)C(O)OR$, $N(R)C(O)R$, $N(R)C(S)R$, $N(R)C(O)N(R)_2$, $N(R)C(S)N(R)_2$, $N(COR)COR$, $N(OR)R$, $C(=NH)N(R)_2$, $C(O)N(OR)R$, or $C(=NOR)R$, wherein R can be hydrogen (in examples that include other carbon atoms) or a carbon-based moiety, and wherein the carbon-based moiety can itself be further substituted.

The term "composition" as used herein refers to a chemical, compound, or substance, or a mixture or combination of two or more such chemicals, compounds, or substances.

The term "solvent" as used herein refers to a liquid that can dissolve a solid, another liquid, or a gas. Non-limiting examples of solvents are silicones, organic compounds, water, alcohols, ionic liquids, and supercritical fluids.

The term "room temperature" as used herein refers to a temperature of about 15° C. to about 28° C.

The term "standard temperature and pressure" as used herein refers to 20° C. and 101 kPa.

As used herein, the term "scum" refers to floatable material skimmed from the surface of primary and secondary settling tanks in wastewater treatment plants. It contains animal fat, vegetable oil, food wastes, plastic material, soaps, waxes and many other impurities discharged from restaurants, households and other facilities.

The term "waste oil," as used herein, refers to oils and/or other lipid-based compositions that are waste byproducts from other processes including, but not limited to, waste oil from wastewater treatment operations (e.g., scum oil), waste oil from food preparation or food product preparation operations, and the like. In particular, "waste oil" can refer to oil and/or lipid-based compositions that include compounds therein that have, until the processes described herein, been difficult to economically process or convert to a value-added product. In an example, a "waste oil" that is treated and converted by the processes described herein is an and/or lipid-based composition that has a high level of free fatty acids in the waste oil, and in particular a free fatty acid content that is high enough to substantially interfere with commercial-grade esterification operations (e.g., acid-catalyzed esterification). In some examples, the terms "high level of free fatty acids" or "high free fatty acid content," when referring to the free fatty acid content in a waste oil, refers to a free fatty acid content in the waste oil that is greater than about 10% (wt FFA/wt waste oil), such as a free fatty acid content that is greater than about 15% (wt/wt), for example a free fatty acid content that is greater than about 20% (wt/wt), greater than about 25% (wt/wt), or greater than about 30% (weight FFA/weight of the waste oil).

Process for Preparing Biodiesel

In various embodiments, processes for the production of biodiesel from one or more waste oils is described herein. In some embodiments, the waste oil includes a high level of free fatty acids therein, e.g., where the high level of free fatty acids can interfere with subsequent processing of the waste oil to convert one or more compounds in the waste oil to biodiesel, such as esterification of the one or more compounds in the waste oil (e.g., acid-based transesterification.). An example of a waste oil that is converted to biodiesel by the processes described herein includes, but is not limited to, a waste oil composition present in a waste byproduct stream in a wastewater treatment process, such as the scum from wastewater treatment processes, which can include a waste oil generally referred to herein as "scum oil."

FIG. 1 shows a flow diagram of an example process 100 for producing a biodiesel prod from a waste oil 102, such as from the scum oil present in scum removed during a wastewater operation. For the sake of brevity, the waste oil 102 may be referred to herein as wastewater scum or scum oil. A person of skill in the art will recognize that the processes described herein, while being particularly useful for conversion of wastewater scum and scum oil to biodiesel, is not limited to scum oil. Rather the person of skill in the art will recognize that other waste oils can benefit from the processes described herein, including the process 100 of FIG. 1. Wastewater scum is a complex material that often includes solids, water, soaps, and oils (referred to herein as "scum oil") and many other impurities. The process 100 includes pretreatment of waste oil 102, such as wastewater scum 102 in order to improve, and in some embodiments, optimize conversion yield. The person of skill in the art will further recognize that other uses of the term "scum" or "scum oil" can be understood as more generally referring to other waste oils. For example, when referring to a "clarified scum" or "clarified scum oil," the person of skill in the art will understand that the same processing step or steps will be more broadly relevant to other "clarified waste oils." Similar references to other types of processed scum or scum oil, such as acidified scum or acidified scum oil, will also be understood as being broadly applicable to similar or identical processing of other waste oils.

Generally, the process 100 for the production of biodiesel comprises (a) separating solids from the waste oil 102 to provide a clarified oil; (b) acidifying the clarified oil to produce an acidified oil composition including free fatty acids derived from the waste oil in the clarified oil; (c) converting at least a portion of the free fatty acids in the acidified oil composition to glycerides to provide a glyceride composition; and (d) reacting at least a portion of the glycerides in the glyceride composition with methanol to form fatty acid methyl ester (FAME) to provide a biodiesel composition.

Separation

The process 100 includes a step of separating 104 a waste oil composition 102, e.g., a wastewater scum 102, to provide a clarified oil composition 106, e.g., a clarified scum 106 and solids 108. In some examples, separating the scum 104 includes separating water 110 that had been present in the wastewater scum 102. In an example, separating the scum 104 includes filtering the wastewater scum 102 to remove the solids 108, which can include, but is not limited to, debris such as plastics, cellulosic biomass, and salts such as undissolved salts. Separating the scum 104 provide a filtered scum, e.g., the clarified scum 106, which includes a scum oil.

Acidification

After separation 104 of the waste oil composition 102, e.g., the wastewater scum 102, in some embodiments, the clarified oil composition 106, e.g., the clarified scum 106, is acidified with an aqueous acid 112. Acidifying the clarified scum 106 with the aqueous acid 112 is also referred to herein as acid washing 114. The acid washing 114 provides an organic fraction comprising free fatty acids (hereinafter "FFAs") derived from the clarified scum 106 and an aqueous fraction. In some embodiments, the aqueous acid 112 used for the acid washing 114 includes, but is not limited to, a strong aqueous mineral acid, such as at least one of sulfuric acid ($H_2SO_4$), hydrochloric acid (HCl), and phosphoric acid ($H_3PO_4$).

In some embodiments, the acid washing 114 converts soap (e.g., $(RCOO^-)_2Ca^{2+}$, $(RCOO^-)_2Mg^{2+}$, or $(RCOO^-)_3$ Al$^{3+}$) to free fatty acids (hereinafter "FFAs") by reacting the soap with the acid 112 to form the FFAs (e.g., RCOOH) and salts. Reaction Equation [1] shows an example of a reaction of soap ((RCOO$^-$)$_2$Ca$^{2+}$ and/or (RCOO$^-$)$_2$Mg$^{2+}$) with sulfuric acid:

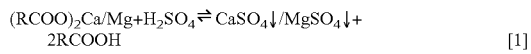

$$(RCOO)_2Ca/Mg + H_2SO_4 \rightleftharpoons CaSO_4\downarrow/MgSO_4\downarrow + 2RCOOH \qquad [1]$$

The acid washing 114 results in the formation of an organic fraction comprising chemicals, compounds, or substances that are relatively insoluble in water, most notably free fatty acids converted from the clarified scum 106. The acid washing 114 also results in the formation of an aqueous fraction of compounds that are relatively soluble in water.

After the acid washing 114, the organic fraction is separated from the aqueous fraction in a second separation 116 to provide a first stream 118 of the organic fraction, referred to hereinafter as "acidified oil composition 118" or simply "acidified oil 118," and a stream 120 of the aqueous fraction, referred to hereinafter as the "acid waste 120." In some embodiments, the acidified oil 118 includes at least about 50 wt. %, 60 wt. %, 70 wt. %, 80 wt. %, or 90 wt. % free fatty acids. In some embodiments, the free fatty acids are about 50-100 wt. %, 60-100 wt. %, 70-100 wt. %, 80-100 wt. %, 90-100%, 60-90 wt. %, or about 70-80 wt. % of the acidified oil 118. In some embodiments, the acid washing 114 and the separation 116 is repeated more than once.

In some embodiments, the separation 116 of at least a portion of the aqueous fraction from the organic fraction, e.g., to provide the acidified oil 118 and the acid waste 120, is performed before one or more steps of converting at least a portion of the free fatty acids in the acidified oil 118 to glycerides, which are described in more detail below. In an example, the separation 116 of the organic fraction from the aqueous fraction, e.g., to provide the acidified oil 118 and the acid waste 120, comprises settling or other separation methods based on density differences between the fractions (e.g., centrifugation).

In some embodiments, the acidification of the clarified scum 106 comprises contacting the clarified scum 106 with the aqueous acid 112, e.g., similar to the acid washing 114 as described above, but also with an organic solvent 122 to provide the organic fraction that includes free fatty acids (e.g., the acidified oil 118) and the aqueous fraction (e.g., the acid waste 120). The contacting of the clarified scum 106 with the aqueous acid 112 and the organic solvent 122 is referred to hereinafter as "acid wash and solvent extraction 124." In some embodiments, the acid wash and solvent extraction 124 provides for solvent-based extraction of organic portions of the clarified scum 106, including components of what can become part of the acidified oil 118.

In some embodiments, at least a portion of the organic solvent 122 can be separated 126 from the organic fraction following the separation 116, referred to hereinafter as "solvent separation 126," to provide the acidified oil 118 and a separated solvent 128. In some embodiments, the solvent separation 126 includes heating the organic fraction from the separation 116 to a temperature of at least 15° C., exposing the organic fraction from the separation 116 to a pressure of about 1 atm or less, or both. The solvent separation 126 of the organic solvent from the organic fraction can be achieved, for example, by rotary evaporation or a similar technique.

In some embodiments, after the solvent separation 126, the free fatty acid content is at least about 50 wt. %, 60 wt. %, 70 wt. %, 80 wt. %, or at least about 90 wt. % of the acidified oil 118. In some embodiments, after the solvent separation 126, the free fatty acids are about 50-100 wt. %, 60-100 wt. %, 70-100 wt. %, 80-100 wt. %, 90-100%, 60-90 wt. %, or about 70-80 wt. % of the acidified oil 118.

In some embodiments, the organic solvent 122 used in the acid wash and solvent extraction 124 is chosen from at least one of hexane, diethyl ether, ethyl acetate, and dichloromethane. The organic solvent can be obtained from a previous acidification separation. In the embodiment shown in FIG. 1, at least a portion of the solvent 122 used for the acid wash and solvent extraction 124 includes recycled separated solvent 128.

In some embodiments, acid washing 114 of the clarified scum 106 includes contacting the clarified scum 106 with the aqueous acid 112, methanol, and glycerol. The methanol and glycerol can be recycled methanol and glycerol obtained from glycerolysis in the glyceride conversion 130 or the separated methanol 144 that is recycled after the transesterification 134, described in more detail below.

In some embodiments, acid washing 114 the clarified scum 106 includes heating the clarified scum 106 and the aqueous acid 112 used in the acid washing 114. Heating the clarified scum 106 and the aqueous acid 112 can occur at a pressure of about 1 atm to about 3 atm, such as 1 atm, 2 atm, or 3 atm.

Conversion to Glycerides

As described above, the process 100 includes converting 130 at least a portion of fatty acids in the acidified oil 118 to glycerides, such as to triglycerides, in order to provide a glyceride composition 132, referred to herein as "glyceride conversion 130." As described in more detail below, the glycerides in the glyceride composition 132 are reacted with methanol to produce fatty acid methyl esters (FAME), which is a primary component of biodiesel.

In some embodiments, the glyceride conversion 130 includes esterification of the free fatty acids in the acidified oil 118, transesterification of the free fatty acids in the acidified oil 118, or both. Methods that can be performed for the glyceride conversion 130 include, but are not limited to: (a) acid-catalyzed esterification; and (b) glycerol esterification, also referred to hereinafter as "glycerolysis."

Acid-Catalyzed Esterification

In some embodiments, the glyceride conversion 130 includes acid-catalyzed esterification, which includes reacting the free fatty acids in the acidified oil 118 with methanol in the presence of an acid to provide water and glycerides (e.g., a mixture of monoglycerides, diglycerides, and triglycerides). In some examples, the acid used for the acid-catalyzed esterification includes, but is not limited to, sulfuric acid. Acid catalyzed esterification is a general approach for the conversion of a process stream that has a high content of free fatty acids, such as the acidified oil 118. In some embodiments, the acid-catalyzed esterification is generally not sensitive to the moisture content of the acidified oil 118 or of the reaction mixture of the methanol, the acid, and the acidified oil 118. Reaction Equation [2] shows an example of the acid-catalyzed esterification of free fatty acids (general formula RCOOH) with methanol (CH$_3$OH):

$$RCOOH + CH_3OH \rightleftharpoons H_2O + RCOOCH_3 \qquad [2]$$

In some embodiments, the acid-catalyzed esterification provided for a reduction in acid value (AV) of the acidified oil 118, which prepares the oils for transesterification 134 (described in more detail below). In some embodiments, the acid-catalyzed esterification reduces the AV to below about 2 mg KOH per g of the glyceride composition 132.

After the reaction of the acid-catalyzed esterification has completed, e.g., after the acid value of the reaction mixture is below about 2 mg KOH per g of the reaction mixture, the reaction mixture can be separated into an organic fraction, e.g., the glyceride composition 132, and an aqueous fraction, e.g., water and unreacted methanol. The glyceride composition 132 is used for the transesterification 134 (described below), and the unreacted methanol from the aqueous fraction can be recycled back to be used as a portion of the methanol for the acid-catalyzed esterification or as at least a portion of the methanol 136 used for the transesterification 134 (described below).

Glycerolysis

In some embodiments, the glyceride conversion 130 includes glycerolysis, which includes reacting the free fatty acids in the acidified oil 118 with glycerol (OHCH$_2$CHOHCH$_2$OH) to form water and glycerides (e.g., a mixture of monoglycerides, diglycerides, and triglycerides). As used herein, the term "glycerolysis" refers to the formation of one or more glycerides from glycerol. In an example, the glycerolysis can include one or more of Reaction Equations [3], [4], and [5];

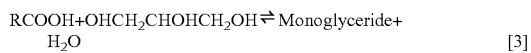  [3]

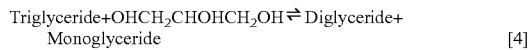  [4]

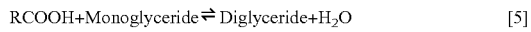  [5]

As the glycerolysis reactions are carried out over time, the resulting reaction mixture can include unreacted fee fatty acids, water, free glycerol, and a mixture of monoglycerides, diglycerides, and triglycerides. The water and the free glycerol can be separated from the monoglycerides, diglycerides, and the triglycerides (referred to collectively herein as "glycerides") to provide a separated glycerol stream and the glyceride composition 132. The glycerol in the separated glycerol stream can be recycled back and used as at least a portion of the glycerol for the glycerolysis. In some embodiments, the glycerolysis is acid catalyzed. In some embodiments, the glycerolysis is base catalyzed.

In some embodiments, at least a portion of the glycerol that is used for the glycerolysis is obtained front the reactions of the transesterification 134, e.g., by reacting at least a portion of the glycerides in the glyceride composition 132 with methanol 136 to form fatty acid methyl ester (FAME) and glycerol. In other words, in some examples, glycerol is a byproduct of the transesterification 134, and the glycerol byproduct can be used for at least a portion of the glycerol for glycerolysis.

In some embodiments, the glycerolysis is conducted at a temperature from about 175-260° C., such as from 200-255° C., for example 220-250° C., such as 230-245° C., for example about 235-240° C., such as about 175° C., about 200° C., about 225° C., about 230° C., about 235° C., about 236° C., about 237° C., about 238° C., about 239° C., about 240° C., about 241° C., about 242° C., about 243° C., about 244° C., about 245° C., about 246° C., about 247° C., about 248° C., about 249° C., about 250° C., about 251° C., about 252° C., about 253° C., about 254° C., about 255° C., about 256° C., about 257° C., about 258° C., about 259° C., or about 260° C.

Conversion to Fatty Acid Methyl Esters (FAME)

In some embodiments, the process 100 includes reacting at least a portion of the glycerides in the glyceride composition 132 with methanol 136 to form fatty acid methyl ester (FAME), which provides a FAME composition 138. In some embodiments, the reaction of the glycerides in the glyceride composition 132 with the methanol 136 is a transesterification reaction 138, referred to hereinafter as "transesterification 134 of the glycerides," or simply "transesterification 134." In some embodiments, the transesterification 134 is a reaction of at least a portion of the glycerides in the glyceride composition 132 with the methanol 136 to produce reaction products and unreacted methanol and glycerides in the glyceride composition 132. In some embodiments, the reaction products include FAME and glycerol.

In some embodiments, the transesterification 134 is performed in the presence of a base catalyst, such as a methoxide catalyst. In some examples, the methoxide catalyst can include, but is not limited to, at least one of: sodium methoxide, potassium methoxide, lithium methoxide, zinc methoxide, calcium methoxide, tributyltin methoxide, magnesium methoxide, tantalum(V) methoxide, titanium(IV) methoxide, antimony(III)methoxide, germanium methoxide, or copper(II) methoxide. In an example, the methoxide catalyst comprises a mixture of two or more of these methoxide compounds.

Biodiesel Finishing

In some embodiments, the process 100 includes further processing of the FAME composition 138 to provide a final biodiesel composition. In some embodiments, further processing of the FAME composition 138 includes separation 140 of methanol and other compounds from the FAME compounds in the FAME composition 138, referred to hereinafter as methanol separation 140, to provide a raw FAME composition 142 and separated methanol 144. In some embodiments, the methanol separation 140 includes contacting the FAME composition 138 with an acid 146 to provide a salt of the methoxide catalyst used in the transesterification 134 and separating methanol and the salt of the methoxide catalyst from the FAME composition 138 to provide the raw FAME composition 142. In some embodiments, the acid 146 for the methanol separation 140 includes, but is not limited to, concentrated H$_2$SO$_4$ (e.g., at least 98% H$_2$SO$_4$). In some embodiments, the methanol separation 140 includes reducing the amount of methanol in the FAME composition 138 by applying a reduced pressure, resulting in the more volatile methanol in the FAME composition 138 being separated as the separated methanol 144.

The separated methanol 144 can be used as at least a portion of the methanol 136 for the transesterification 134. In other words, the methanol 136 used for the transesterification 134 can comprise unreacted and separated methanol 144 that is being recycled from a previous batch or cycle. In some embodiments, the separated methanol 144 is recycled and combined with fresh methanol 136 for use in the transesterification 134.

In some embodiments, the further processing of the FAME composition 138' can include separation 148 of the glycerol from a FAME composition, such as the FAME composition 138 or the raw FAME composition 142, to provide a purified FAME composition purified FAME composition 150. In some embodiments, the glycerol separation 148 includes separating a raw glycerol composition 152 from the raw FAME composition 142 to provide a purified FAME composition 150. The raw glycerol composition 152 can include glycerol and a portion of the unreacted methanol from the FAME composition 138 that was not separated by the methanol separation 140.

In theory, FAME and glycerol are immiscible and will readily separate into an organic fraction comprising mainly the FAME and an aqueous fraction comprising the glycerol, water, and unreacted methanol. However, it has been found that in some embodiments, one or more components in the scum oil being recovered from the wastewater scum 102 results in the formation of a stable single-phase system. It is suspected that the compound or compounds responsible for the single-phase behavior act as a surfactant that increases inter-solubility of the glycerol and the FAME so that separation of these compounds becomes more difficult. However, it has been found that adding additional relatively-pure glycerol 154 to the raw FAME composition 142 as part of the glycerol separation 148 leads to improved separation of glycerol and FAME compounds from the raw FAME composition 142 to provide for a more purified FAME composition 150. The process of adding additional glycerol 154 is referred to herein as applying a "glycerol wash" to the raw FAME composition 142 to better enable the glycerol separation 148 in order to provide the more pure form of the FAME compounds in the purified FAME composition 150. It was also found that the glycerol wash with the relatively pure glycerol 154 can wash out some of the base catalyst from the transesterification 134, e.g., a methoxide catalyst. In some embodiments, contacting the raw FAME composition 142 with the extra glycerol 154 for the glycerol wash also removes other impurities from the raw FAME composition 142 that may have otherwise ended up in the final biodiesel composition.

In some embodiments, the raw glycerol composition 152 from the glycerol separation 148 can be processed or purified to provide a recycled glycerol 156 that can be used for other parts of the process 100. In an embodiment, the raw glycerol composition 152 is separated into the relatively pure recycled glycerol 156 and a waste glycerol 158 that is discarded. In some embodiments, the recycled glycerol 156 is used to form at least a part of the glycerol 154 for the glycerol wash.

In some embodiments, the further processing of the FAME composition 138 includes purifying a biodiesel composition, such as the raw FAME composition 142 or the purified FAME composition 150, with respect to the one or more FAME compounds therein to produce a biodiesel product composition 160. In some embodiments, the purification to provide the biodiesel product composition 160 can include distillation 162 of the purified FAME composition 150. In some embodiments, the distillation 162 can be repeated two or more times.

In some embodiments, purification with respect to FAME to provide the biodiesel product composition 160 includes water washing 164 the purified FAME composition 150. The water washing 164 can include, for example, adding water to the purified FAME composition 150 and allowing the mixture to settle into an aqueous fraction and an organic fraction and, subsequently, isolating or separating the organic fraction from the aqueous fraction to provide the biodiesel product composition 160. In some embodiments, the water washing 164 can include, after removing the organic fraction from the resulting mixture, drying the organic fraction at a pressure of 1 atm or less, also referred to as "vacuum drying," to drive off trace amounts of water from the organic fraction in order to provide the biodiesel product composition 160 with a minimal amount of water present.

Sulfur Reduction

Figure 2:
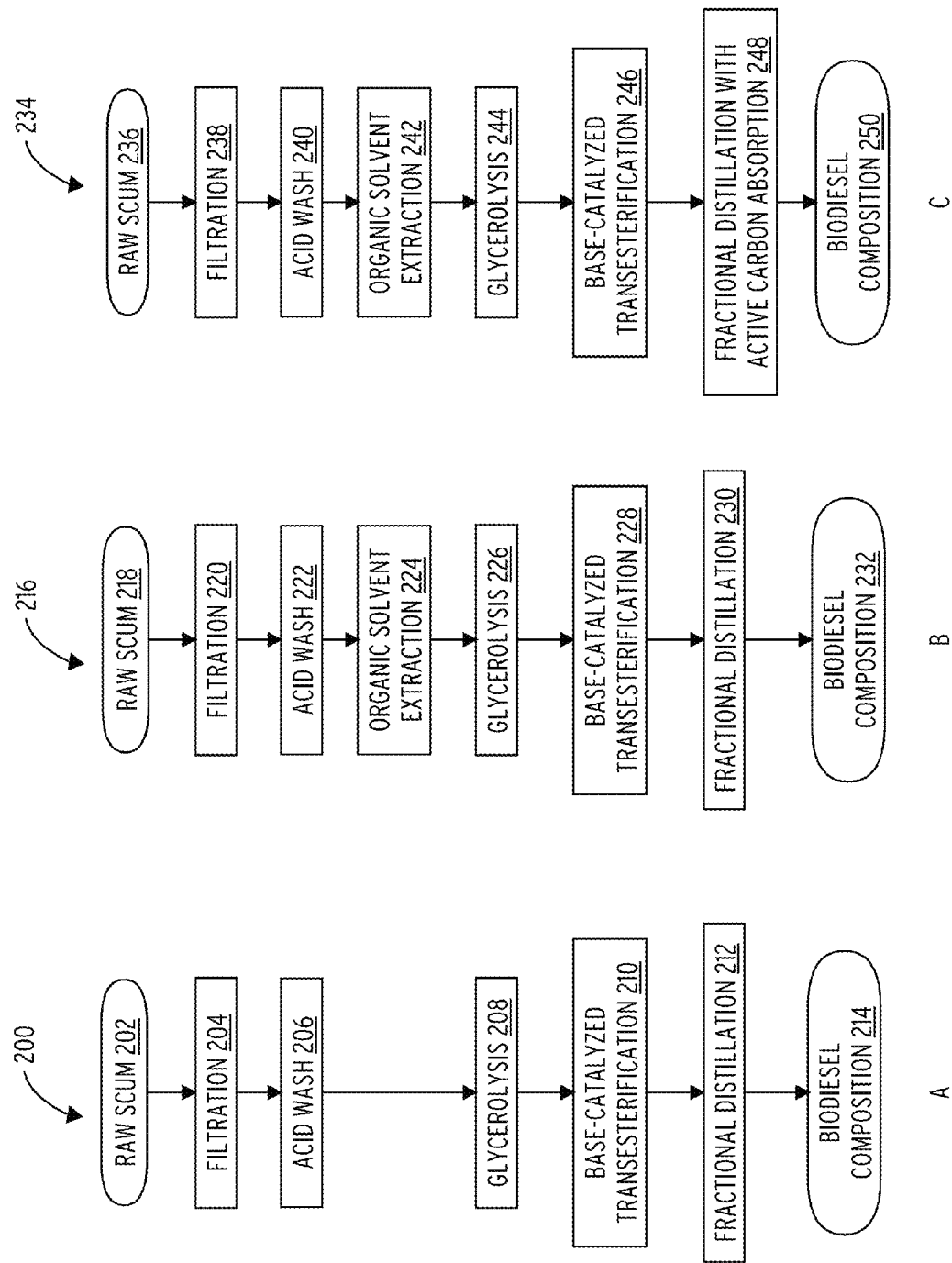
FIGS. 2A-2C show flow diagrams of three alternative examples of processes for converting scum to biodiesel.

FIGS. 2A-2C show examples of process steps for the conversion of scum, such as wastewater scum, to a biodiesel composition. FIGS. 2A-2C show different alternatives for processing the scum. In particular, the examples of FIGS. 2A-2C show methods of reducing sulfur content in the final biodiesel composition.

FIG. 2A shows a flow diagram of an example process 200 for converting a waste oil composition 202, such as raw scum 202 from a wastewater treatment facility, to a biodiesel composition 214. In various embodiments, the raw scum 202 is filtered 204 to separate solids from a clarified oil composition, such as a scum oil. The clarified scum oil is then subjected to an acid wash 206, which results in an acidified oil composition, e.g., an acidified scum oil. The acidified oil is then subjected to a process of glycerol esterification, also referred to as glycerolysis 208, to convert free fatty acids in the acidified oil to glycerides in order to provide a glyceride-rich oil composition, e.g., a glyceride-rich scum oil. Note that there is no additional extraction step between the acid wash 206 and the glycerolysis 208, such as an extraction with an organic solvent.

The glyceride-rich oil composition is then subjected to base-catalyzed transesterification 210 to convert the glycerides to fatty acid methyl esters (FAME), which provides a crude FAME composition. The crude FAME composition is then purified via fractional distillation 212 to provide the final biodiesel composition 214. The distillation column used for the fractional distillation 212 is packed with conventional distillation column packing, such as steel wools, which provides for the desired contact between liquid/solution phases and gaseous phases during the fractional distillation 212.

FIG. 2B shows a flow diagram of another example process 216 for converting a waste oil composition 218, such as a raw scum 218, to a biodiesel composition 232. In various embodiments, the raw scum 218 is filtered 220 to separate solids from a clarified oil composition, such as a clarified scum oil. The clarified oil is then subjected to an acid wash which results in an acidified oil composition, such as an acidified scum oil. The acidified oil is then contacted with an organic solvent, such as heptane, in an organic solvent extraction 224, to provide a solvent-extracted acidified oil composition, such as a solvent-extracted acidified scum oil. In some embodiments, the organic solvent extraction 224 removes impurities from the acidified oil and result in a higher quality final biodiesel composition 232. In some examples, the organic solvent extraction 224 provides for good extraction of sulfur from the acidified oil and provides for the biodiesel composition 232 having reduced sulfur compared to the biodiesel composition 214 produced by the similar process 200.

In some embodiments, the organic solvent used for the organic solvent extraction 224 is a non-polar organic solvent. In an embodiment, the organic solvent used in the organic solvent extraction 224 is one or more of petroleum ether, hexane, or heptane. As discussed below with respect to EXAMPLE 2.3, in some examples, heptane is preferred because it has been found that heptane is more effective at removing sulfur from the process stream (see, e.g., FIG. 8).

After contacting the acidified oil with the organic solvent in the organic solvent extraction 224, at least a portion of the organic solvent may still be present as part of a solvent-extracted oil composition-solvent mixture (e.g., an organic phase). In some embodiments, the organic solvent is removed from oil-solvent mixture by stripping the solvent from the solvent-extracted oil compositions at low pressures (e.g., vacuum pressure) or high temperatures, or both. In an example, the solvent-extracted oil-solvent mixture is exposed to a temperature of at least about 100° C. and a pressure of 2.5 mm Hg or less, or both.

The solvent-extracted acidified oil is then subjected to glycerolysis 226 to convert free fatty acids in the solvent-extracted acidified oil to glycerides in order to provide a glyceride-rich oil composition, such as a glyceride-rich scum oil. The glyceride-rich oil is then subjected to base-catalyzed transesterification 228 to convert the glycerides to fatty acid methyl esters (FAME), which provides a crude FAME composition. The crude FAME composition is then purified via fractional distillation 230 to provide the final biodiesel composition 232. The distillation column used for the fractional distillation 230 can be similar or identical to that used in the fractional distillation 212 of the process 200. For example, the column for the fractional distillation 230 can be packed with conventional distillation column packing, such as steel wools, which provides for the desired contact between liquid/solution phases and gaseous phases during the fractional distillation 230.

As can be seen from a comparison of FIGS. 2A and 2B, the process 216 is similar to the process 200 of FIG. 2A, except that the process 216 includes the organic solvent extraction 224 between the acid wash 222 and the glycerolysis 226. The organic solvent extraction 224 provides for the removal of certain impurities from the process stream, most notably sulfur. In an example, the organic solvent extraction 224 results in a sulfur content in the final biodiesel composition 232 that is lower than the sulfur content of a process that is identical to the process 216 but without the organic solvent extraction 224. In some embodiments, the organic solvent extraction 224 provides for a higher quality biodiesel composition 232 from the process 216 compared to the biodiesel composition 214 from the process 200.

FIG. 2C shows a flow diagram of another example process 234 for converting a waste oil composition 236, e.g., a raw scum 236 to a biodiesel composition 250. In various embodiments, the waste oil composition 236, e.g., the raw scum 236, is filtered 238 to separate solids from a clarified oil composition, e.g., a clarified scum oil. The clarified oil is then subjected to an acid wash 240, which results in an acidified oil composition, e.g., an acidified scum oil. The acidified oil is then contacted with an organic solvent, such as heptane, in an organic solvent extraction 242, to provide a solvent-extracted acidified oil composition, e.g., a solvent-extracted acidified scum oil. Like the organic solvent extraction 224 of the process 216, in some embodiments, the organic solvent extraction 242 removes impurities from the acidified oil, such as sulfur, which results in a higher quality final biodiesel composition 250. The solvent-extracted acidified oil is then subjected to glycerolysis 244 to convert free fatty acids in the solvent-extracted acidified oil to glycerides in order to provide a glyceride-rich oil composition, e.g., a glyceride-rich scum oil. The glyceride-rich oil is then subjected to base-catalyzed transesterification 246 to convert the glycerides to fatty acid methyl esters (FAME), which provides a crude FAME composition. The crude FAME composition is then purified via fractional distillation 248 to provide the final biodiesel composition 250.

The distillation column used for the fractional distillation 248 in the process 234 can be similar to the columns used for the fractional distillation 212 in the process 200 in FIG. 2A or for the fractional distillation 230 in the process 216 of FIG. 2B. For example, the column for the fractional distillation 248 can be packed with conventional distillation column packing, such as steel wools, which provides for the desired contact between liquid/solution phases and gaseous phases during the fractional distillation 248. However, in some embodiments, the distillation column that is used for the fractional distillation 248 is slightly modified compared to the column used for the fractional distillation 212 (FIG. 2A) or for the fractional distillation 230 (FIG. 2B). In an example, the column used for the fractional distillation 248 is packed not only with the conventional packing described above, e.g., steel wools, but is also packed with an active carbon absorption medium that can further absorb impurities, such as sulfur, from the process stream during the fractional distillation 248. In an example, the active carbon pack in the distillation column is a sludge-activated carbon. In an example, the mass of the active carbon loaded in the distillation column is sufficient to remove impurities, most notably sulfur, from the crude FAME composition being distilled in the fractional distillation 248. In an example, the active carbon is loaded at about 10% of the weight of the crude FAME composition in the distillation column during the fractional distillation 248.

The fractional distillation 248 in a column that includes active carbon provides for the removal of certain impurities from the process stream, most notably sulfur, to result in a higher quality biodiesel composition 250 for the process 234 compared to the biodiesel composition 214 of the process 200 or the biodiesel composition 232 of the process 216. In an example, the organic solvent extraction 242 and the fractional distillation 248 results in a sulfur content in the final biodiesel composition 250 that is lower than the sulfur content of a process that is identical to the process 234 but without the organic solvent extraction 242 and the fractional distillation 248. In an example, the fractional distillation 248 results in a sulfur content in the final biodiesel composition 250 that is lower than the sulfur content of a process that is identical to the process 234 but without the fractional distillation 248.

EXAMPLES

Various embodiments of the present disclosure can be better understood by reference to the following EXAMPLES, which are offered by way of illustration. The present invention is not limited to the EXAMPLES given herein.

Materials

The wastewater scum samples were collected from the Metro Plant at St. Paul, Minn., USA. Sulfuric acid (96.4%, AR) and hydrochloric acid (36.5-38.0%, AR) were obtained from Mallinckrodt Baker, Inc. Paris, Ky., USA. Phosphoric acid (85.0%, GR) was obtained from EMD Millipore Corp. (formerly EMD Chemicals, Inc.), Billerica, Mass., USA. Potassium methoxide (>90.0%) was obtained from Alfa Aesar, Haverhill, Mass., USA. Butylated hydroxytoluene (BHT), methanol (anhydrous, 99.8%), chloroform (99.8%), and diethyl ether (99.7%) were obtained from MiliporeSigma (formerly Sigma-Aldrich, Inc.), St. Louis, Mo., USA. BF$_3$-methanol reagent (14% borontrifluoride, 86% methanol), sodium hydroxide 0.5 normal in methanol, heptane (HPLC grade), and glycerol (99.9%) were obtained from Thermo Fisher Scientific, Inc., Waltham, Mass., USA. Potassium hydroxide concentrate (1.0 mol/L) was obtained from Fluka Analytical, a division of MiliporeSigma (formerly Sigma-Aldrich, Inc.), St. Louis, Mo., USA. Ethanol (200 proof) was obtained from Decors Laboratories, Inc., King of Prussia, Pa., USA. Distilled water was obtained from Premium Waters, Inc., Minneapolis, Minn., USA.

Example 1: First Example Process for Conversion of Wastewater Scum to Biodiesel

Example 1 Overview

To begin, large particles in the wastewater scum were separated by filtration. Subsequently, acid washing was performed followed by gravitational settling. This was done to convert soap (e.g., $RC(O)O^-)_2Ca^{2+}$ and $(RC(O)O^-)_3Al^{3+}$)

to free fatty acid (FFA), to separate oil from water and water soluble/insoluble electrolytes, and to further remove fine particles. Next, the upper layer oil (e.g., upper fraction) was collected and subjected to acid catalyzed esterification and then a base catalyzed transesterification processes to form fatty acid methyl esters (FAME). The basic reactions are described in Reaction Equations [6]-[8].

$$\text{Soap} + \text{Acid} \rightarrow \text{Salt} + FFA \quad [6]$$

$$FFA + \text{Methanol} \xrightarrow{Acid\ Catalyst} \text{Water} + FAME \quad [7]$$

$$\text{Triglyceride} + \text{Methanol} \xrightarrow{Base\ Catalyst} \text{Glycerol} + FAME \quad [8]$$

Thereafter, a glycerol washing was performed to aid in separating the glycerol and other impurities from the FAME. After separating the glycerol and methanol from the FAME, the crude FAME was then refined by fractional distillation to produce high grade biodiesel that may be directly used in diesel engines.

Example 1.1: Filtration

Scum oil was obtained in solid form at room temperature. It melted at about 40° C. (depending on its components) and the viscosity of scum was negatively related with the temperature. For easing the separation of the scum oil from solid particles and at the same time drying the oil, a filtration process was conducted under a relative high temperature to reduce the viscosity of the scum oil. In a drying oven of 105° C., 157 g of scum was loaded into a polyester mesh filter bag with pore size of 100 microns and a beaker was placed beneath the filter bag to receive the oil melted from the scum sample. The filtering process lasted for 24 hours. Weights of filtered oil and remaining solids were collected every 15 min during the first 8 hrs and at the end point of 24 hrs. The moisture content was calculated by subtracting the oil and solid weights from the total scum weight.

Figure 3:
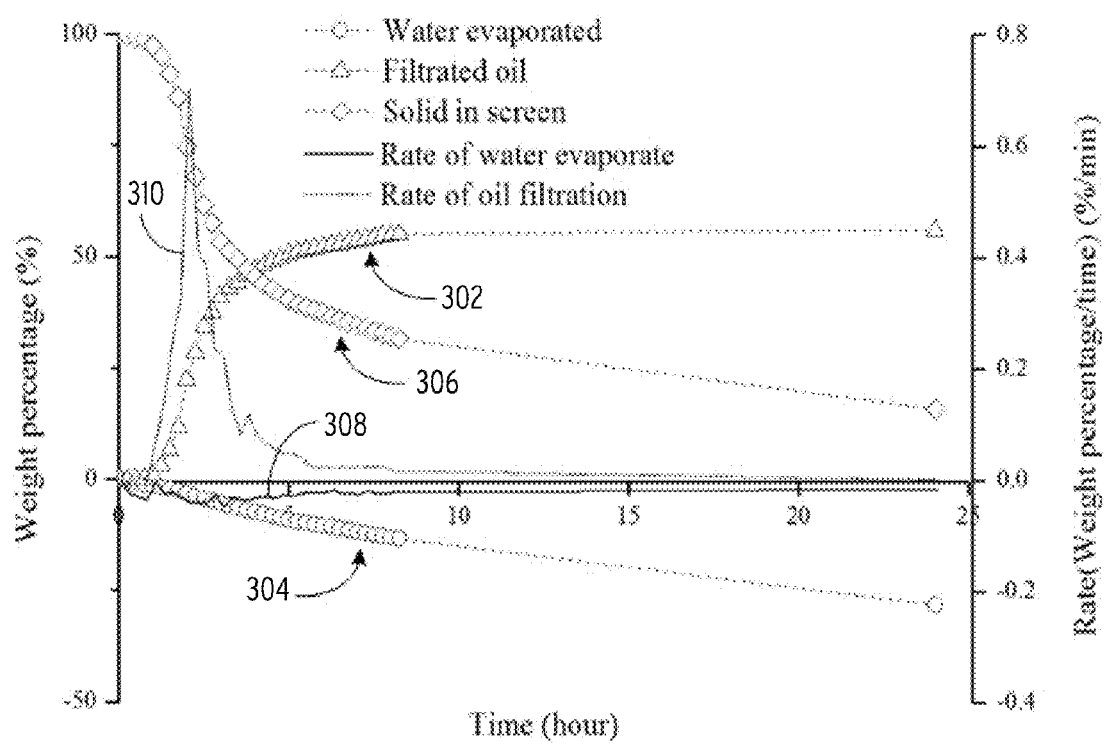
FIG. 3 illustrates a weight distribution and rate curve for the filtering of scum in a process for converting the scum to biodiesel.

At the end of the process, water, oil, and solids amounted 28.2%, 56.0%, and 15.8% of the total scum weight, respectively. The specific filtering curves of the filtering of EXAMPLE 1.1 are illustrated in FIG. 3, which shows the recorded weight (% of total scum weight) over time of the filtered oil 302, the evaporated water 304, and the solids 306 left in the filter bag. As can be seen in FIG. 3, the weight content of the water 304 started to decline during the first 15 minutes and the total evaporated water 304 at 24 hours was about 28.2% of the scum weight. The solid line 208 in the FIG. 3 indicates the water evaporation rate over time. FIG. 3 shows that the highest water-evaporation rate 308 was about 0.041% per minute observed at about 2.5 hours. The water-evaporation rate 308 declined to below 0.023% per minute after about 5.75 hours. Filtered oil 302 was received in the beaker, continuously increasing to reach about 56.0%, after 24 hours. The rate of oil filtration curve, represented by the dashed line 210 in FIG. 3, was a derivative of the weight percentage of filtered oil 302 over time. The oil-filtration rate 310 was very low during the first hour, then increased to the maximum of about 0.702% per minute at about 2 hours. Subsequently, the oil-filtration rate 310 rate decreased to below 0.023% per minute after about 5.75 hours. The weight of the solids 306 in the filter bag is also shown in FIG. 3. The curve for the solids 306 drops from 100% to about 15.8% indicating about 15.8% of the total solids originally present in the scum were left in the scum after filtering. The curvature of the solids 306 is negatively correlated to the curve for the oil 302 during about the first six (6) hours, which indicates that the weight loss of scum solids 306 is mainly due to the separated oil 302. During the time from about 6 hours to about 24 hours the curve of solids 306 is positively related to the curve for water 304, which indicates that the weight loss of the solids 306 from the scum during about 6 hours to about 24 hours was mainly due to the evaporation of the water 304.

At the time of about 6 hours, the filtered oil 302 is about 52.2% of the total scum weight in the filter bag, which represents about 93.2% of the total oil in the scum before filtering. However, at a time of about 8 hours, 98.0% of the total oil (54.9% of total scum weight) had been filtered out.

Example 1.2: Acid Washing

The filtered scum oil from EXAMPLE 1.1 was subjected to acid washing. Some purposes for the acid washing include one or more of, and in some examples all of: conversion of any soap in the scum to free fatty acids; maximizing the biodiesel production yield; breaking emulsions in the scum oil for better water/oil separation; and further removing impurities from the scum oil. The acid washing also was found to make acid catalyzed esterification (EXAMPLE 1.3) easier, as there was less impurity interference with the reactants. $H_2SO_4$, HCl, and $H_3PO_4$, with two $H^+$ strength 0.2 N and 1.2 N in water were compared for the scum oil acid washing pretreatment. The ratio of the scum oil to the acid solution, by weight, was about 1:1. The filtered scum oil from EXAMPLE 1.1 was mixed with the acid solution in a set of flasks with condensers on top. A magnetic stirring water bath was applied to offer stirring power and keep the temperature of the reaction system at about 60° C. After contacting the filtered scum oil with the acid solution for about 1 hour, the mixture was allowed to settle and for about a half hour (30 minutes) so that the mixture could separate into an upper phase or upper fraction, which included acidified scum oil, and a lower phase or lower fraction, which included water, acid, and sediment. The upper phase or upper fraction was separated and isolated from the lower phase or lower fraction to provide an acidified scum oil.

It was found that an acid solution with 0.2 N was unable to sufficiently acidized the filtered scum oil. An acid solution with 1.2 N was found to be able to acidize scum oil completely, leaving 0.3-0.4 mol/L $H^+$ surplus after the acid treatment. It was observed that most sediment was formed when sulfuric acid ($H_2SO_4$) was used as the acid. Some sediment was found to form when phosphoric acid ($H_3PO_4$) is used. No sediment appeared when hydrochloric acid (HCl) was used for the acid washing. It is believed that this is due to $SO_4^{2-}$ and $PO_4^{3-}$ ions being more likely to form insoluble salts with the metallic elements that may be present in the scum oil, such as $CaSO_4$, $Fe_2(SO4)_3$, and so on. When using dried and filtered scum oil as the starting material, the acid washing was found to account for 10% of mass loss due to removal of these metallic impurities by sedimentation.

Samples from the acid washing of EXAMPLE 1.2 were submitted to Soil Testing & Research Analytical Laboratory at the University of Minnesota (St. Paul, Minn., USA) to perform elemental analysis. An inductively coupled plasma atomic emission spectrometer (Perkin Elmer Optima 3000, USA) was applied on all the samples to provide a total elemental analysis of the acidified scum oil samples.

Table 1 shows the major impurity elements in the scum oil before and after acid washing.

TABLE 1

Element analysis of raw scum oil before and after acid washing.

| mg/kg | Filtered Scum oil | $H_2SO_4$ | HCl | $H_3PO_4$ |
|---|---|---|---|---|
| Metallic Elements | | | | |
| Ca | 1483.2 ± 18.1[a] | <0.43[b] | <0.43[b] | 12.18 ± 1.06[c] |
| Fe | 189.2 ± 3.1[a] | 5.08 ± 0.57[b] | 3.03 ± 0.58[b] | 23.61 ± 0.48[c] |
| Al | 109.4 ± 2.4[a] | 7.78 ± 3.49[b] | 8.18 ± 1.85[b] | 14.74 ± 0.90[b] |
| Mg | 58.9 ± 1.2[a] | <0.18[b] | <0.18[b] | <0.18[b] |
| Zn | 55.4 ± 0.8[a] | 0.80 ± 0.00[b] | 4.41 ± 2.73[b,c] | 6.82 ± 0.76[c] |
| Mn | 14.6 ± 0.3[a] | <0.08[b] | <0.08[b] | 0.48 ± 0.00[c] |
| K | 10.05 ± 1.63[a] | 0.66 ± 0.06[b] | <0.30[c] | <0.30[c] |
| Cu | 5.28 ± 0.15[a] | 1.66 ± 0.11[b] | 0.62 ± 0.10[c] | 3.73 ± 0.06[d] |
| Pb | 3.49 ± 0.04[a] | 1.22 ± 0.07[b] | <0.18[c] | <0.18[c] |
| Na | 2.03 ± 0.11[a] | <0.13[b] | <0.13[b] | <0.13[b] |
| Non-Metallic Elements | | | | |
| N | 1990 ± 20[a] | 1200 ± 10[b] | 1490 ± 0[c] | 1590 ± 10[d] |
| S | 613 ± 7[a] | 613 ± 20[a] | 540 ± 5[b] | 540 ± 10[b] |
| P | 13.3 ± 0.3[a] | 1.02 ± 0.11[b] | 0.76 ± 0.12[b] | 13.65 ± 0.67[a] |

[a-d]values in horizontal with different superscripts were significant different ($p < 0.05$).

Many soap component elements (e.g., calcium, iron, aluminum, magnesium, zinc) were decreased or eliminated after acid washing. For example, $Ca^{2+}$ dropped from 1483 mg/kg in the filtered scum oil to less than 0.43 mg/kg after acid washing. Nitrogen content is an indicator of surfactant content as it may form active hydrophilic groups and surfactants, such as $-NH^3$, $-N_2^+$, and the like. After $H_2SO_4$ treatment, the nitrogen content dropped from 1990 mg/kg to 1200 mg/kg, which was significantly superior to HCl and $H_3PO_4$. Table 1 demonstrates that $H_2SO_4$ seems to be the most suitable acid washing reagent for the scum oil acid washing pretreatment.

The acid washing was more effective for removing inorganic impurities than for those organic compounds containing nitrogen (N), phosphorous (P), and sulfur (S). After the acid washing, nitrogen content still remained at 1200 mg/Kg in scum. Eighty percent (80%) of the sulfur was not affected. Only phosphorous was mostly removed. These organic impurities might interfere with subsequent processes. In some examples, 6% sulfuric acid solution mixed with scum oil with 1:1 ratio by weight was used for the acid washing.

Example 1.3: Acid-Catalyzed Esterification

For a feedstock high in free fatty acids (FFA), such as the acidified scum oil from EXAMPLE 1.2, acid-catalyzed esterification followed by base-catalyzed transesterification has generally been used where the acid catalyzed esterification became a sort of "pretreatment" to reduce the FFA in the feedstock to the base-catalyzed transesterification.

After the acid washing of EXAMPLE 1.2, the acidified scum oil contained residual water and had an average acid value ("AV") of 21 mg $KOH \cdot g^{-1}$ oil. Acid value, measured as mg KOH/g of the oil sample being analyzed, is an indicator of the free fatty acid content in the scum oil. ASTM D1980-87 (1998) ("Standard Test Methods for Acid Value of Fatty Acids and Polymerized Fatty Acids") were used to determine the acid value. By monitoring changes of acid value during acid-catalyzed esterification process, progress of reaction was determined.

The acid-catalyzed esterification reduced the acid value to below 2 mg $KOH \cdot g^{-1}$ oil through the acid-catalyzed esterification reaction described above in Reaction Equation [7] to form a glyceride composition comprising a mixture of one or more glyceride compounds. The reduction in AV of the scum oil and the conversion to the glyceride composition further prepares the scum oil for the base-catalyzed transesterification of EXAMPLE 1.4. In the biodiesel industry, the AV of a feedstock, particularly one with a high fatty acid content, is preferably reduced below 2 mg $KOH \cdot g^{-1}$ oil before the base-catalyzed transesterification.

The acid-catalyzed esterification of EXAMPLE 1.3 included combining methanol (30% of oil weight), sulfuric acid (3% and 5% of oil weight), and the acidified scum oil produced from EXAMPLE 1.2 in a flask with a condenser at the top. A magnetic stirring water bath was applied to offer stirring power and to keep the temperature of the reaction system at about 60° C. The acid value of oil phase in the flask was monitored every 15 minutes during the first hour of reaction, and after 150 minutes.

After the reaction was determined to be complete, the mixture was allowed to settle for one hour so that the reaction mixture could separate into an upper organic phase and a lower aqueous phase. The upper phase included layer of scum oil that included one or more glycerides, referred to hereinafter as "glyceride-rich scum oil". The lower phase include a majority of the unreacted methanol and all of the acid fed to the flask in EXAMPLE 1.3.

The glyceride-rich scum oil layer was separated and isolated from the lower phase and dried at 105° C. in oven overnight to remove any residual water and other volatiles. The dried glyceride-rich scum oil was used as the feedstock for the base-catalyzed transesterification reaction of EXAMPLE 1.4, described below.

Figure 4:
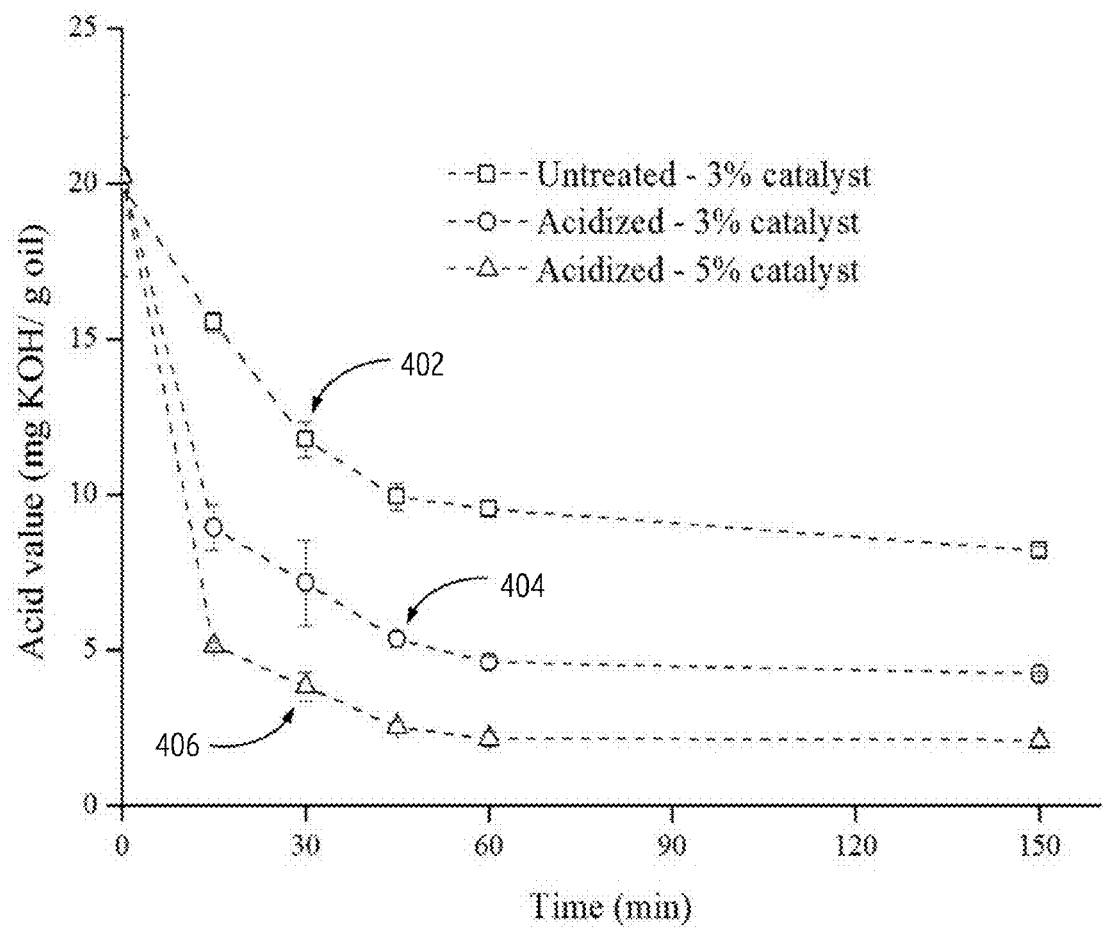
FIG. 4 illustrates the acid value over time under various conditions during an acid-catalyzed esterification reaction in a process for converting a scum to biodiesel.

FIG. 4 is a chart of the acid value over time during the acid-catalyzed esterification of EXAMPLE 1.3 under various conditions. FIG. 4 shows the decrease of the acid value for three different oil samples under various concentrations of $H_2SO_4$. The curve 402 represents the change in acid value for an non-acid treated scum oil sample, e.g., the filtered scum oil from EXAMPLE 1.1 without having be subjected to the acid washing of EXAMPLE 1.2. The non-acid washed oil sample corresponding to the curve 402 was reacted in the presence of a 3% solution of $H_2SO_4$. The curve 404 and the curve 406 represent the change in acid value for samples of the acidified scum oil from EXAMPLE 1.2 (e.g., scum oil after having been subjected to acid washing) being reacted in the presence of a 3% $H_2SO_4$ solution and a 5% $H_2SO_4$ solution, respectively. FIG. 4 shows that the acid values of all three experiments decreased during acid-catalyzed esterification. The acid value curve 402 for the non-acid washed scum oil sample reacted with 3% catalyst decreased at the slowest rate and had a final acid value of 8.07 mg $KOH \cdot g^{-1}$ oil. In comparison, the acid value curve 406 for the acid-washed scum oil sample reacted with 5% catalyst decreased at the fastest rate and had a final acid value of 2.10 mg $KOH \cdot g^{-1}$ oil. The acid value curve 404 for the acid-washed scum oil sample reacted with 3% catalyst decreased at rate close to that of the curve 406 for the acid-washed sample reacted with 5% catalyst, although not quite as fast, and had a final acid value of 4.27 mg $KOH \cdot g^{-1}$ oil.

As shown in FIG. 4, the acid-catalyzed esterification for the non-acid washed scum oil, represented by the curve 402, was not as complete as with the acid-washed scum oil reacted with the same amount of catalyst admixture, as represented by the curve 404. The inventors theorize that this may be due, at least in part, by the sulfuric acid reacting with soaps in the filtered scum oil and due to produced water. It is believed that the sulfuric acid consumed when reacted with the soaps in the curve 402 reduced the catalyst strength. It is also believed that the additional water also hindered the esterification reaction because esterification is a reversible reaction and water is one of the reaction products. As such, the acid-washed scum oil represented by the curve 404 had better performance during the esterification reaction than the non-acid washed scum oil represented by the curve 402. It was also found that the acid-washed scum oil sample reacted with 5% catalyst, represented by the curve 406, was able to achieve a desired acid value from the acid-catalyzed esterification reaction, e.g., of about 2 mg $KOH \cdot g^{-1}$ oil or less.

Figure 5:
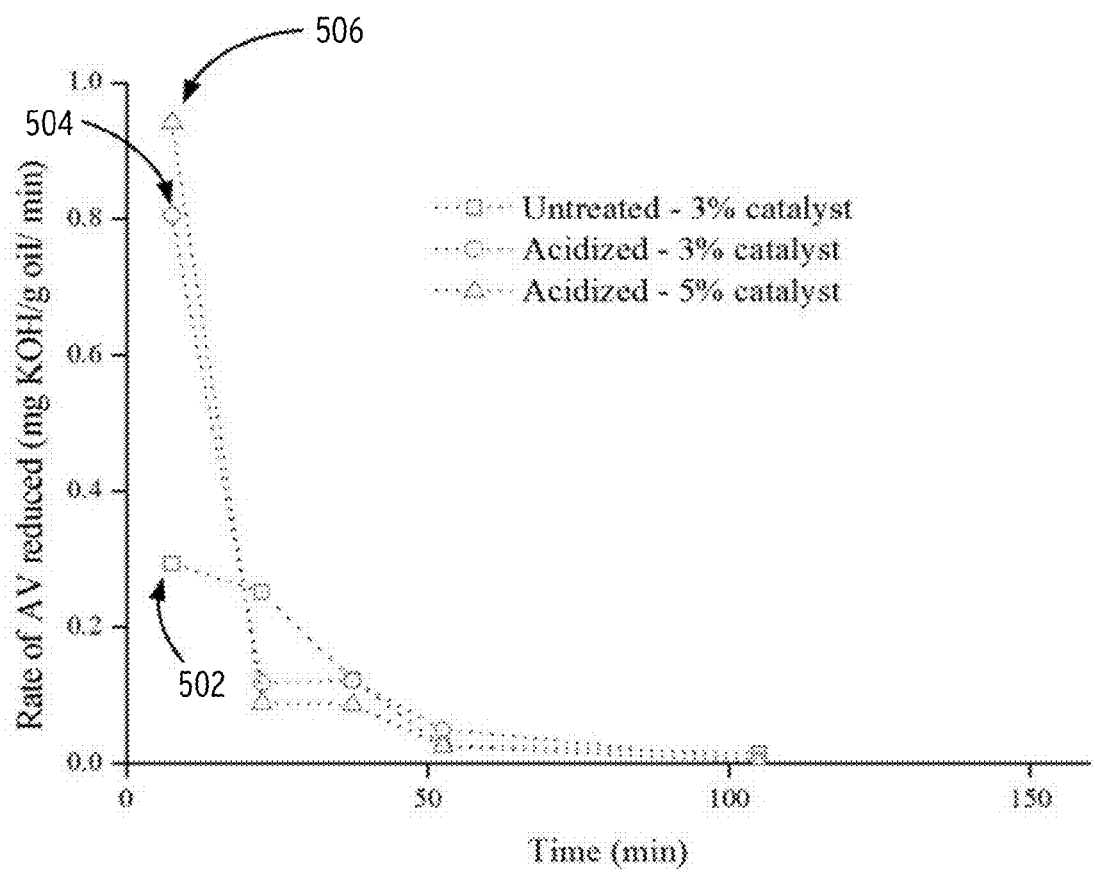
FIG. 5 illustrates the rate of acid value reduction over time under various conditions during an acid-catalyzed esterification reaction in a process for converting a scum to biodiesel.

FIG. 5 is a chart showing the rate of acid value reduction under the same conditions as in FIG. 4. FIG. 5 shows the rate as a derivative of the acid value over time. In FIG. 5, the curve 502 corresponds to the non-acid washed oil sample reacted with 3% catalyst, the curve 504 corresponds to the acid-washed oil sample reacted with 3% catalyst, and the curve 506 corresponds to the acid-washed oil sample reacted with 5% catalyst. In other words, the curve 502 is the rate of reduction for the same non-acid washed oil sample as curve 402, the curve 504 is the rate of reduction for the same acid-washed oil sample reacted with 3% catalyst as the curve 404, and the curve 506 is the rate of reduction for the same acid-washed oil sample reacted with 5% catalyst as the curve 406.

As can be seen in FIG. 5, the reaction rates of all three experiments decreases as time elapses, which indicates that the acid-catalyzed esterification reactions achieve equilibrium gradually. During the first 15 minutes, the reaction rate of the acid-washed scum oil samples e.g., 0.94 mg $KOH \cdot g^{-1}$ oil$\cdot min^{-1}$ for the curve 506 (5% catalyst) and 0.81 mg $KOH \cdot g^{-1}$ oil$\cdot min^{-1}$ for the curve 504 (3% catalyst)) is much higher than for the non-acid washed scum oil (e.g., 0.29 mg $KOH \cdot g^{-1}$ oil$\cdot min^{-1}$ for the curve 502). The reaction rates were found to decrease more rapidly in the next quarter of hour for the acid-washed oil samples of curve 504 and curve 506. After 1 h, the reaction rate of all three samples dropped below 0.05 mg $KOH \cdot g^{-1}$ oil$\cdot min^{-1}$. Therefore, the inventors hypothesize that it is reasonable to set the duration of the acid-catalyzed esterification at around 1 hour. Based on these results, the acid-catalyzed esterification was found to have the best result when 5% oil weight of $H_2SO_4$ is used as catalyst and 30% oil weight of methanol is used to react with scum oil at 60° C. for 1 hour.

Example 1.4: Base-Catalyzed Transesterification

The reactor used for the base-catalyzed transesterification of EXAMPLE 1.4 was as same as that described above for the acid-catalyzed esterification of EXAMPLE 1.2. Methanol (30% of oil weight) was contacted with the glyceride-rich scum oil obtained from EXAMPLE 1.3 to form a raw FAME composition. Potassium methoxide ($CH_3OK$, 0.5% and 1% of oil weight) was used as a catalyst. Samples of the reaction mixture were collected every 10 minutes for an hour. For analyzing the content of fatty acid methyl esters (FAME), the methanol left in samples was flash evaporated first, and then the glycerol washing procedure described in EXAMPLE 1.5 was applied to induce separation of the glycerol and the FAME. The supernatant containing the FAME was analyzed by gas chromatography-mass spectrometry ("GC-MS") analysis.

Figure 6:
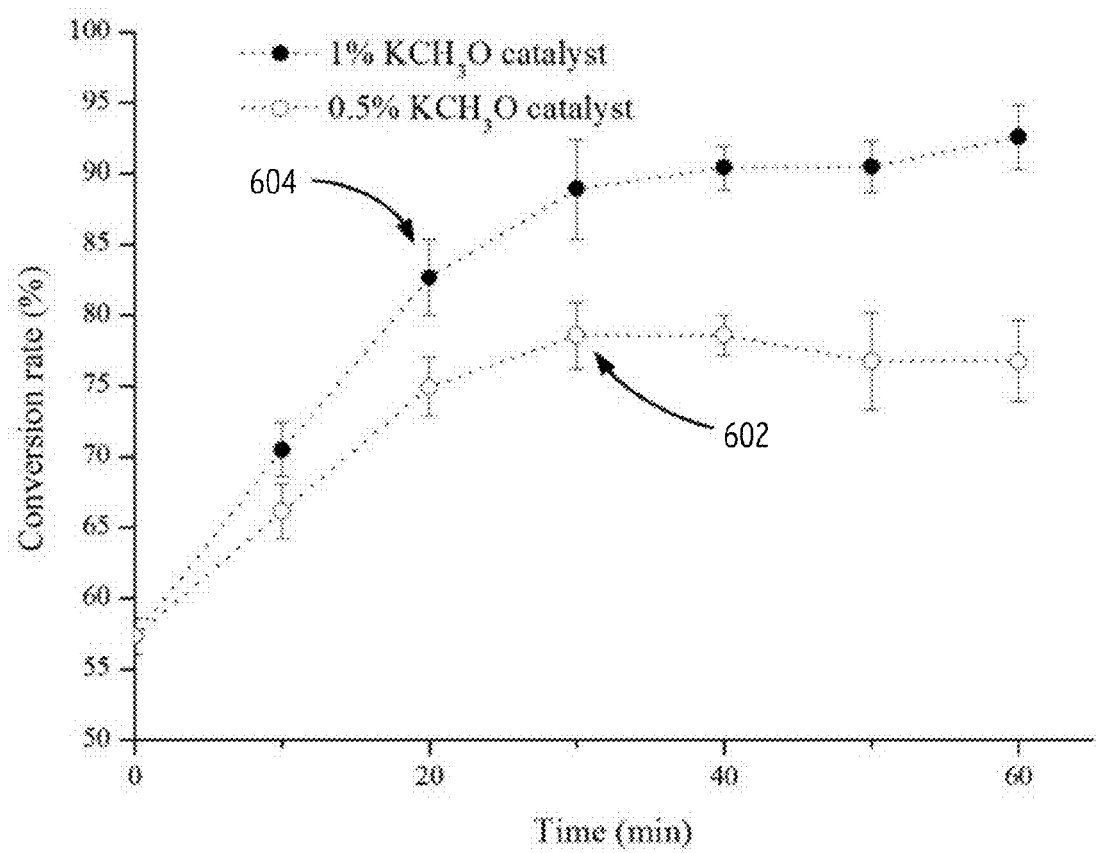
FIG. 6 illustrates the effect of the amount of base catalyst on the conversion rate over time during a base-catalyzed transesterification reaction in a process for converting a scum to biodiesel.

FIG. 6 is a graph showing the effect of the amount of base catalyst on the conversion rate over time for the base-catalyzed transesterification reaction of EXAMPLE 1.4. The curve 602 shows the conversion rate for transesterification of a glyceride-rich scum oil sample reacted in the presence of 0.5% potassium methoxide catalyst ($CH_3OK$). The curve 604 shows the conversion rates of a similar glyceride-rich scum oil sample in the presence of 1% $CH_3OK$. The conversion rates of both samples increase during the first half hour, and after 30 minutes, reach a plateau. Therefore, the inventors hypothesize that a reasonable duration for the base-catalyzed transesterification reaction (60° C., 30% methanol) is about 30 minutes to ensure reaction reaches equilibrium. The final conversion rate of the scum oil sample with reacted 1% $CH_3OK$, represented by the curve 604, was 92.6%, which indicates the ratio of produced FAME to raw oil used in base catalyze reaction, on a weight basis. For the scum oil sample reacted with 0.5% $CH_3OK$, represented by the curve 602, the conversion rate was 76.7%. Potassium methoxide showed strong basicity in methanol. For instance, a scum oil sample with an acid value of 3 mg $KOH \cdot g^{-1}$ oil will consume 0.3% KOH (of oil weight). Hence, much less catalyst will be utilized. This phenomenon was also observed when the base catalyst was less than 0.5%. In an example, for the base-catalyzed transesterification reaction, a highly suitable condition tested was using 1% (of the scum oil weight) of $CH_3OK$ (as catalyst and 30% (of the scum oil weight) of methanol to react with a glyceride-rich scum oil at 60° C. for 30 minutes.

Example 1.5: Glycerol Washing and Layering

In principle, methyl esters of fatty acids and glycerol are immiscible. When using a better quality feedstock, such as pure or relatively pure soybean oil, the FAME and glycerol separate into two layers by gravity settling after the base-catalyzed transesterification reaction. However, the raw FAME composition from EXAMPLE 1.4 has been found to form a stable single-phase system even after 24 hours settling at 60° C. The inventors hypothesize that some organic compounds in the scum, and that remain in the raw FAME composition, such as surfactants or other impurities and soaps, increase the inter-solubility of glycerol and FAME in the raw FAME composition, such that the glycerol could not be separated.

Separation of the product mixture and removal of the base catalyst is preferred before further purification or finishing of the raw FAME composition, such as via distillation. Otherwise, the compounds in the raw FAME composition can undergo reverse reaction and re-saponification. It was discovered by the inventors that by adding extra glycerol to the raw FAME composition, separation of the FAME and glycerol was actually improve. Therefore, a process step that the inventors refer to as "glycerol washing" was employed. The glycerol washing not only allows the oil mixture to separate and form distinct phase layers but also provides for the removal of much of the base catalyst and other impurities still present in the raw FAME composition in order to provide a crude FAME composition.

After the base-catalyzed transesterification reaction of EXAMPLE 1.4, the methanol in the raw FAME composition was removed by rotary evaporation (e.g., under reduced pressure). glycerol was then added into multiple samples of the raw FAME composition (with methanol removed), with each sample having varying different ratio of the glycerol relative to the raw FAME composition, e.g., 1:20; 1:10; 1:5; 1:1.33; 1:2; and 1:1, by weight. Each sample was mixed thoroughly by magnetic stirring at 60° C. for 20 minutes. The samples were allowed to settle for 12 hours at the 60° C. temperature. In each sample, after settle, the upper phase layer included mainly FAME and the lower phase layer included mainly glycerol and base catalyst.

Figure 7:
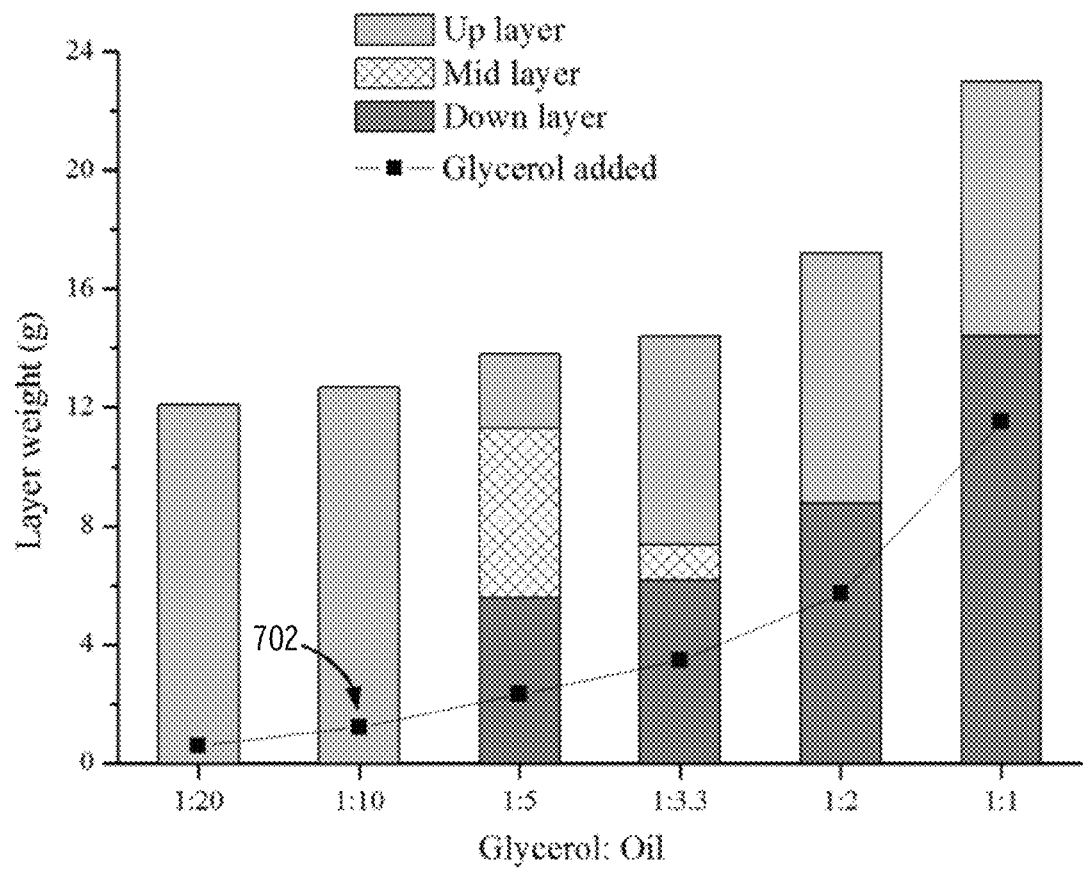
FIG. 7 illustrates the effect of glycerol-to-oil ratio on layering in a glycerol washing step of a process for converting a scum to biodiesel.

FIG. 7 illustrates how different amounts of glycerol addition affected the phase layering of the resulting mixture. The samples (11.5 g) for EXAMPLE 1.5 were collected from the reaction product of the base-catalyzed transesterification reaction of EXAMPLE 1.4 and part of methanol from each sample was removed by evaporation. The bars along the x-axis of the chart in FIG. 7 indicate the ratio of additional glycerol to the mixture oil of the raw FAME composition samples. The y-axis of the chart in FIG. 7 depicts the weight of each layer and the relative position of boundary layers between phases. FIG. 7 illustrates that below a glycerol:FAME composition ratio of about 1:5, the mixture seems to remain a one-phase system. From the ratios of 1:5-1:3.3, the raw FAME composition separates into three phase layers: an upper phase layer (indicated by the light gray portion of the bar), a lower phase layer (indicated by the dark gray portion of the bar), and a boundary layer (indicated by the cross-hatched portion of the bar, if present). For samples at ratios of 1:5-1:3.3, the upper phase layer (light gray) mainly comprised FAME, while the middle layer (crosshatched) and the lower layer (dark gray) were mixtures of glycerol and FAME. Samples with ratios of 1:2 and 1:1 resulted in two phase-layer separation with the upper FAME phase (light gray) and the lower glycerol phase (dark gray) being completely separated. The curve 702 with the square-dot data points illustrates the weight of the glycerol admixture. As can be seen in FIG. 7, the weight of the glycerol layer (dark gray lower layer) was more than the weight of glycerol added. This demonstrates that adding extra glycerol to the raw FAME composition caused the glycerol in the raw FAME composition to separate from the FAME compounds.

The final glycerol layer (dark gray lower layers included KOH (from $CH_3OK$), pigments, and other impurities that readily dissolved in the glycerol. During the glycerol washing of EXAMPLE 1.5, many impurities leached into the glycerol phase. The upper phase layer comprising the FAME compounds (light gray bar) still contained some impurities, but those impurities can mostly be removed by distillation. Notably, KOH had a high solubility in glycerol phase (>16%, w/w, 60° C.); however, in the methyl ester phase the value was as low as less than 0.2%. This indicates that KOH has a strong tendency to remain in glycerol phase rather than with the FAME phase after separation. For the glycerol washing step, one preferred condition involves adding one part of glycerol to two parts of raw FAME composition and washing the remaining glycerol and other impurities out of the resulting crude FAME composition.

Example 1.6: Distillation

The crude FAME composition of the upper phase layer of the glycerol-ash from EXAMPLE 1.5 was found to have about 90% FAME (according to the base catalyzed condition). The crude FAME composition was introduced to a customized vacuum rectification distillation column and a refined FAME composition was obtained that can be used as a biodiesel composition.

During distillation, the bottom temperature was increased from 142-210° C., and top temperature was increased from 120-160° C. The vacuum varied between 0.3-0.4 mm Hg. The distillation yield was 88.2%).

Analysis of Biodiesel Produced from Scum (Process of Example 1)

The biodiesel composition obtained from the distillation of EXAMPLE 1.6 was analyzed with gas chromatography. The $BF_3$ catalysis method was applied from AOCS Official Method Ce 2-66 (1997). This method proposes excess reactant and excess catalyst to make sure that all the fatty acid in sample was transformed into FAME.

FAME in all samples was analyzed by GC-MS using the method described in Li et al., "Integration of algae cultivation as biodiesel production feedstock with municipal wastewater treatment: strains screening and significance evaluation of environmental factors," Bioresour. Technol., 102, 10861-67 (2011). Oil samples (about 100 mg) were weighed into 10 ml volumetric flasks and diluted with chloroform to 10 ml. The GC-MS (Agilent 7890-5975C, USA) equipped with a HP-5 column and a mass detector was used. Chromatographic data were recorded and addressed by a built-in Agilent data analysis software. Components were identified in NIST Mass Spectral Database. Quantification was carried out by comparing the peak area with that of the GLC-10 and GLC-30 standard mixtures (Sigma-Aldrich, Co.).

The majority of FAMEs in the biodiesel composition formed with different fatty acids were C14, C16 and C18. The weight percentages of each FAME were as follows: C14:0 (5.63%), C16:0 (32.45%), C16:1 (2.27%), C18:0 (15.59%), C18.1 and C18:2 (41.35%), and other (2.7%). Among all, octadecanoic acid (C18) and hexadecenoic acid (C16), which were the main components of the produced biodiesel composition, accounted for 91.66%. Saturated fatty acid (SFA) accounted for 53.67%—much higher than refined vegetable oil biodiesel, which, other than biodiesel produced from palm oil, tends to be from about 6.5-5.79%. A higher SFA percentage leads to a higher Cetane number (CN) and higher cloud point. A higher CN can indicate improved combustion performance of the biodiesel composition.

Biodiesel Yield and Fuel Quality

When using dried and filtered scum oil as the starting material, the acid washing of EXAMPLE 1.2 resulted in about a 90% yield. The combination of the acid-catalyzed esterification (EXAMPLE 1.3), the base-catalyzed transesterification (EXAMPLE 1.4), and the glycerol washing (EXAMPLE 1.5) resulted in about an 89% yield. The distillation (EXAMPLE 1.6) resulted in about an 88% yield.

As a result, the total biodiesel yield from the dried and filtered scum oil resulting from EXAMPLE 1 was about 70%, which is equivalent to about 1.24 ton per day biodiesel production or about 134,000 gallon biodiesel per year for the St. Paul Metro Plant. Based on the biodiesel B100 selling price in the Twin Cities, Minn. (Minneapolis and St. Paul) that ranged from $3.8-$4.9 in 2014, the potential biodiesel production could bring about $518,000-$668,000 revenue to the Metro Plant at Saint Paul, Minn.

The distilled biodiesel fuel was sent out and tested by Iowa Central Fuel Testing Laboratory (Fort Dodge, Iowa) using ASTM D 6751/BQ-9000 (Full Spec Test Package for B100). The results are shown in Table 2, which provides the fuel quality of the distilled biodiesel composition output from EXAMPLE 1; except for the sulfur content, total acid number, and oxidation stability, the biodiesel composition output from EXAMPLE 1 passed all ASTM specifications.

TABLE 2

Biodiesel Product Analysis

| Test | Method | Result | Unit | ASTM limit | Pass/Fail |
|---|---|---|---|---|---|
| Calcium & Magnesium | EN14538 | 0.0 | ppm | 5, max | Pass |
| Flash point, Closed cup | D93 | 176.0 | ° C. | 93, min | Pass |
| Alcohol Control: | | | | | |
| Option1: Methanol | EN14110 | | mass % | 0.2, max | N/A |
| Option2: Flash point | D93 | 1760. | ° C. | 130, min | Pass |
| Water and Sediment | D2709 | <0.005 | % volume | 0.050, max | Pass |
| Kinematic Viscosity cSt@40° C. | D445 | 4.941 | mm2/sec | 1.9-6.0 | Pass |
| Sulfated Ash | D874 | 0.001 | % mass | 0.020, max | Pass |
| Sulfur | D5453 | 33.6 | ppm | 15, max | Fail |
| Copper Corrosion at 50° C. | D130 | 1A | n/a | No. 3, Max | Pass |
| Cloud Point | D2500 | 13 | ° C. | Report | Report |
| Carbon Residue | D4530 | 0.000 | % mass | 0.050, max | Pass |
| Total Acid Number | D664 | 1.43 | mgKOH/g | 0.50, max | Fail |
| Cold Soak Filterability | D7501 | 114 | seconds | 360, max* | Report |
| Free Glycerin | D6584 | 0.000 | % mass | 0.020, max | Pass |
| Total Glycerin: | D6584 | 0.002 | % mass | 0.240, max | Pass |
| Monoglycerides | D6584 | 0.000 | % mass | n/a | |
| Diglycerides | D6584 | 0.014 | % mass | n/a | |
| Triglycerides | D6584 | 0.000 | % mass | n/a | |
| Phosphorus | D4951 | 0.000000 | % mass | 0.001, max | Pass |
| Distillation at 90% rec., ATE | D1160 | 351.7 | ° C. | 360, max | Pass |
| Sodium & Potassium | EN14538 | 0.1 | ppm | 5, max | Pass |
| Oxidation Stability | EN15751 | 0.1 | hours | 3, min | Fail |
| Visual Inspection | D4176 | 1 | haze | 2 | Pass |

*360 max for Grade 2B, 200 max for Grade 1B, with max 0.400 for monoglycerides

The sulfur content of the biodiesel composition was 33.6 ppm (about twice the ASTM limit). Therefore, it appears that using sulfuric acid in the acid washing process (EXAMPLE 1.4) does not reduce the sulfur content effectively (see Table 1, above). Ion exchange resins or magnesium silicate powder as absorbent may reduce the sulfur content after the refining process.

The total acid number of the biodiesel composition was 1.43 (about three times higher than the ASTM limit). In the batch distillation process used in EXAMPLE 1.8, the acid number of samples from different distillation stages increased when distillation was progressing. It is believed that this was due to the temperature rise. The last 5% of the distillate contained the highest total acid value (>10 mg KOH/g oil) and the acid value of the front 95% of the distillate had acid values lower than the standard (<0.4 mg KOH/g oil). An effective way to reduce total acid value may be to collect the last 5% output and neutralize it separately.

The oxidation stability of the biodiesel composition was 0.1 hour, which is far lower than the standard value. However, the addition of antioxidant may be able to raise the oxidation stability and solve this issue easily.

Example 2: Second Example Process for Conversion of Wastewater Scum to Biodiesel Example 2.1: Scum Filtration 2606.5 grams of raw scum was heated to 180° F. in a 4 L beaker, then combined with an acidic waste water stream (e.g., water from the acidulation and water wash of EXAMPLE 2.2, described below) at a 2:1 ratio. The raw scum was then pumped through a primary screen filter (~5 mm) to remove woody biomass, organic conglomerates and plastics from the oil. A secondary bag filter (~500 microns can be applied in series, if needed, to purify the oil further.

Approximately 79% of the raw scum was separated as a liquid scum oil and water mixture. After being dried at 250° F. and 100 mmHg for 5 minutes, the scum oil fraction yielded 1413.3 grams, a 54% oil extraction efficiency relative to the raw starting material.

Example 2.2: Acidulation and Water Wash

Starting with 1113.0 grams of the filtered and undried scum oil from EXAMPLE 2.1, a combination of 55.0 grams (5.0% wt/wt) of 98% sulfuric acid and 556.0 grams deionized water (2:1 oil to water) was charged to the oil at 150° F. The temperature of the mixture was maintained while being mixed thoroughly with an agitator for 30 minutes. Afterwards, the mixing was slowed significantly and the mixture allowed to settle for 30 minutes. After settling, the acidic water and a white precipitate was decanted from the bottom of the reaction vessel.

A second water wash using 50% wt/wt deionized water was added to the oil at 150° F. and mixed for 15 minutes. Any residual mineral acid in the oil was dissolved in the water and was then decanted after 30 minutes of settling with slight agitation.

The resulting oil was a free fatty acid (FFA) rich oil that now represents approximately 92% (1028.8 grams) of the initial filtered wet scum oil, wt/wt.

Example 2.3: Solvent Extraction

Solvent extraction was applied to further remove impurities from the FFA-rich scum oil of EXAMPLE 2.2 and to improve final biodiesel quality. The solvent extraction also made the esterification (EXAMPLE 2.4) and transesterification (EXAMPLE 2.5) easier due to less impurity interference with the reactants. Based on the weight of acidified FFA-rich scum oil obtained from the acid washing of EXAMPLE 2.2, 50% wt/wt heptane, hexane, or petroleum ether and 30% wt/wt of water were added to the acidified oil, respectively. The extraction mixture was maintained in a 3-necked round-bottom flask at 338 K for 1 h, and the flask was affixed with condenser, agitator and thermometer. After 30 min of settling, the bottom acidic water phase and middle slightly polar hydrophobic regions were decanted as wastes while the top layer of solvent and oil was removed to a rotary evaporator for solvent distillation. The solvent distillation process was carried out at 373 K and 2.5 mmHg. Under the high temperature and vacuum condition, solvent was easily recycled.

After solvent distillation, the sulfur concentrations of the oil samples were measured using ultraviolet fluorescence as described in Section 2.3.3. A desulphurization rate (ΔS %) was calculated by Equation [9]:

$$\Delta S\ (\%) = (S_0 - S_1)/S_0 \times 100\% \quad [9]$$

where $S_0$ and $S_1$ are the sulfur concentrations of the oil samples before and after solvent extraction, respectively.

Figure 8:
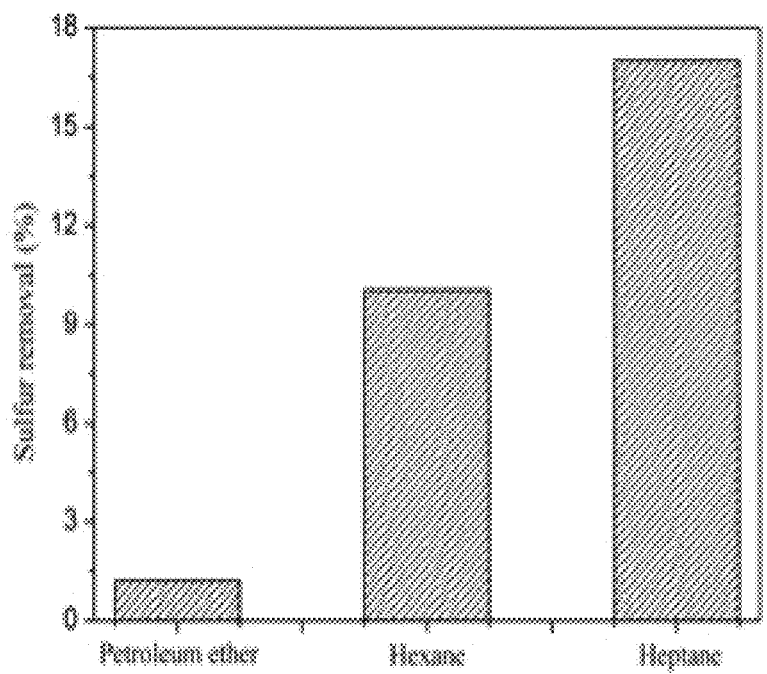
FIG. 8 illustrates the effectiveness of various solvents for the purpose of removing sulfur from a processing stream during a process for converting a scum to biodiesel

Various organic solvents such as petroleum ether, hexane, and heptane were tested in solvent extraction process. The desulphurization rates were calculated based on the changes of sulfur content in scum liquid before and after solvent extraction. As can be seen in FIG. 8, different solvents had different influences on the desulfurization rates. Almost 17% of sulfur-containing compound was removed when using heptane as the organic solvent, which was higher than that of hexane (10%) and petroleum ether (1.2%). The inventors hypothesize that this may be caused by the different polarities of solvents. As a non-polar solvent, heptane has higher solubility towards non-polar molecules in the scum oil. Low-polarity or non-polar compounds, like triglycerides, and can more readily dissolve in heptane solution while compounds with high polarity, sulphoxides and sulphones, remained in the water phase.

In an example, the acid-washed scum oil is heated to approximately 120° F. while slowly agitating in a 3 L flask. Heptane ($C_7H_{16}$) was added to the mixture at 30% (wt/wt) to act as an organic solvent, or 308.6 grams of heptane charged to the 1028.8 grams of scum oil available. In addition, 20% (wt/wt) of deionized water was charged at the same time as the heptane solvent and the total mixture was allowed to agitate for 30 min at 120° F.

After the 30 min of agitation was complete, the mixture was allowed to settle without agitation for 30 minutes while the temperature was maintained at 120° F. After which time the lowest two phase components, a mixture of water and polar hydrophobic compounds, were passively removed through the bottom of a separatory funnel.

The heptane solvent suspended in the oil was removed via vacuum stripping at low pressures. Using the same reaction vessel used for the next step of the process, the glycerolysis of EXAMPLE 2.4, the scum oil-heptane mixture was heated to a temperature above 250° F. Once the liquid mixture reached 250° F., a vacuum was applied to the reaction vessel until a final pressure of 35 mm Hg was obtained and maintained for 10 minutes. Vaporized heptane was carried out of the reaction vessel and condensed using chilled water (60° F.) in a separate collection chamber. The resulting extracted scum oil was a FFA-rich and glyceride-rich dry product that can be immediately glycerized without issue.

Example 2.4: Glycerolysis/Glycerol Esterification

The 1028.8 grams of the extracted scum oil from EXAMPLE 2.3 was heated to 460° F. while being agitated inside an inert nitrogen environment. Nitrogen was introduced subsurface and aided in the removal of water through top mounted side ports on the reaction vessel. During the heating process, water and volatile organic compounds were vaporized from the extracted scum oil and carried out of the reaction vessel before being recaptured using a chilled water condenser.

When the extracted scum oil reached 460° F., 185.2 grams (18% wt/wt) of U.S.P. glycerol was charged to the extracted scum oil under inert conditions. The reaction mixture was stirred vigorously for 3 hours while maintaining a temperature of 460° F. Heat was removed after 3 hours and the nitrogen was removed once the temperature of the extracted scum oil and glycerol reaction mixture fell below 300° F. After the reaction, 1121.3 grams of the resulting glycerol-esterified scum oil was cooled to below 200° F. and an acid value (AV) of less than 1.0 mg KOH/g of the glycerol-esterified scum oil was determined using a wet chemistry titration. Thus, less than 0.5% Free Fatty Acid remained in the glycerol-esterified oil after the glycerolysis of EXAMPLE 2.4.

Example 2.5: Transesterification

The 1121.3 grams of glycerol-esterified scum oil from the glycerolysis of EXAMPLE 2.4 was cooled to 170° F. in a reaction vessel fixed with a top mounted reflux condenser. A combination of methanol and sodium methoxide was charged to the glycerol-esterified scum oil and brought to reflux temperature and reacted for 1 hour. Methanol was charged at 2.5 stoichiometric equivalents to the free fatty acid in the glycerol-esterified scum oil. 30% sodium methoxide was charged at 0.625% wt/wt relative to the glycerol-esterified scum oil. After a 1 hour reaction period, heat was removed and agitation was slowed significantly to allow for a faster separation of glycerol-methanol phase and a biodiesel composition phase. After 1 hour of settling at 135° F., 295.5 grams of a glycerol-methanol mixture was decanted from the bottom of the reaction vessel.

Example 2.6: Catalyst Neutralization and Filtration of Glycerol

After decanting of the 295.5 grams of glycerol-methanol mixture, the amount of sodium methoxide ($NaOCH_3$) catalyst present in the mixture was determined using a wet chemistry titration method. Sulfuric acid ($H_2SO_4$) was added to the decanted glycerol-methanol mixture in order to neutralize the NaOCH$_3$ catalyst (e.g., to bring the pH to about 7-9), forming Na$_2$SO$_4$ and MeOH in the process. 3.9 grams of H$_2$SO$_4$ was used to neutralize the NaOCH$_3$ catalyst while mixing, which brought the pH down from an initial 10.4 to a final 8.4 after neutralization. Due to a lower solubility of Na$_2$SO$_4$ in the presence of MeOH, the glycerol was filtered through course filter to remove salt and conglomerated organic scum precipitated during the neutralization reaction. This filtration effectively removes salts and impurities from the glycerol, allowing it to be saturated a second time after being charged back to the biodiesel composition and mixed.

Example 2.7: Vacuum Stripping, Glycerol Wash, and Decant

The neutralized glycerol was recombined with the biodiesel composition from the transesterification for a total of 1418.2 grams of a glycerol-biodiesel mixture. The glycerol-biodiesel mixture was heated to 250° F. in a reaction vessel and a vacuum of 65 mmHg was applied for 5 minutes to remove excess methanol from the glycerol-biodiesel mixture. The methanol was condensed in a separate flask between the reaction vessel and the vacuum pump using a chilled water system.

After the vacuum stripping was complete, a resulting 1219.0 grams of the glycerol-biodiesel mixture were allowed to physically decant under slight agitation. After 1 hour of decanting, 183.8 grams of glycerol was removed from the bottom of the vessel, leaving 1021.4 grams of a vacuum-stripped biodiesel composition.

Residual biodiesel in the reactor was subjected to a 15% U.S.P. glycerol wash at 105° F. while mixing, to further remove sulfur and color impurities. After 10 minutes of mixing, the glycerol-residual biodiesel solution was allowed to settle, and free glycerin was decanted from bottom of the vessel.

Example 2.8: Biodiesel Distillation

The 1021.4 grams of the vacuum-stripped biodiesel was then distilled through a packed column with a 2:1 reflux rate. The distillation reaction reached 460° F. with 2.0 mm Hg, producing 816.8 grams (80%) of distilled biodiesel. The distillation bottoms accounted for less than 20%, or under 200.0 grams, of residual material. Any unaccounted for material was attributed to incondensable volatile organics.

Example 2.9: Glycerol Sink Trap

One system modification to the distillation unit is the addition of a "glycerol sink trap" in the methyl ester condenser. The sink trap is at an intentionally low point in the distillation column, such as a tube or chamber whose volume is based roughly on the amount of free glycerol estimated in the undistilled biodiesel composition. The sink trap removes free glycerol unintentionally carried over in a localized low point in the condenser where the denser glycerol phase can settle without being carried over into the receiving vessel. The glycerol sink trap also allows for the lighter biodiesel phase to flow freely over the top. The glycerol sink trap can effectively lessen the burden of the subsequent water wash stage of EXAMPLE 2.11 to remove all remaining free glycerol.

Example 2.10: Active Carbon Packed Distillation Column for Sulfur Reduction

In addition to the distillation process described in EXAMPLE 2.8, the distillation column can be packed with active carbon in addition to the packing materials used to facilitate the distillation, e.g., steel wools. In an example, the active carbon loaded in the distillation column is a sludge-activated carbon loaded in the column at 10% of the vacuum-stripped biodiesel. The active carbon absorbs sulfur from the biodiesel composition being processed by the distillation column to result in a lower sulfur content in the distilled biodiesel composition.

The reduction in sulfur provided for by the active carbon was tested by conducting preparing three batches of biodiesel from processes along the lines of EXAMPLE 2. For a first batch, identified as Batch I, the raw scum was subjected to the filtration of EXAMPLE 2.1, the acidulation and water wash of EXAMPLE 2.2, the glycerolysis of EXAMPLE 2.4, the transesterification of EXAMPLE 2.5, the catalyst neutralization and glycerol filtering of EXAMPLE 2.6, the vacuum stripping and glycerol washing of EXAMPLE 2.7, and the biodiesel distillation (without active carbon) of EXAMPLE 2.8 without the solvent extraction of EXAMPLE 2.3. In this way, the process for preparing Batch I is substantially similar to the process 200 described above with respect to FIG. 2A.

For a second batch, identified as Batch II, the process was substantially the same as for Batch I, but with the addition of the heptane solvent extraction of EXAMPLE 2.3 to remove sulfur after the acidulation and water wash of EXAMPLE 2.2 but before the glycerolysis of EXAMPLE 2.4. In this way, the process for preparing Batch II is substantially similar to the process 216 described above with respect to FIG. 2B.

For a third batch, identified as Batch III, the process was substantially the same as Batch II, but instead of using just the packing material, e.g., steel wools, in the distillation column, the distillation column is also packed with sludge-activated carbon (10% of oil weight) of this EXAMPLE 2.10 to further remove sulfur. In this way, the process for preparing Batch III is substantially similar to the process 234 described above with respect to FIG. 2C.

The refined biodiesel compositions from Batches I, II, and III were collected in different temperature ranges (463-473 K, 473-483 K, 483-493 K, and 493-518 K). The sulfur compounds, sulfur contents and FAME content in the three samples were analyzed by ultraviolet fluorescence and GC-MS techniques, respectively. The results, shown below in Table 3, show that the active carbon packed distillation column can reduce sulfur content below the ASTM standard of 15 ppm.

TABLE 3

Comparison of Sulfur Content in Biodiesel Production

| Samples | Sulfur contents (ppm) | | |
|---|---|---|---|
|  | Batch I* | Batch II | Batch III |
| Biodiesel (180-200° C.) | 66.3 | 33.4 | 58.5 |
| Biodiesel (200-210° C.) | 12.1 | 11.7 | 8.9 |
| Biodiesel (210-220° C.) | 7.4 | 12.3 | 9.6 |
| Biodiesel (220-246° C.) | 21.2 | 47.9 | 18.2 |
| Biodiesel (180-246° C.) | 24.15 (Fail) | 21.8 (Fail) | 13.29 (Pass) |
| ASTM limit |  | ≤15 |  |

*The sulfur content of biodiesel made via a process ousing acid-catalyzed esterification, rather than glycerolysis, and base-catalyzed transesterification was 33.6 ppm.

Example 2.11: Water Wash and Vacuum Dry

The 816.8 grams of distilled biodiesel from the distillation of EXAMPLE 2.8 was water washed at 135° F. for 10 minutes while mixing, using 20% wt/wt deionized water. After the 10 minutes of water washing, the agitation was halted to allow for phase separation and the water phase was decanted from the bottom of the vessel.

The biodiesel phase was heated to 250° F. at 65 mm Hg for 10 min. Residual water was driven out of the biodiesel composition and out of the reactor to be condensed in a separate flask using chilled water. Leaving behind 771.2 grams of B100-quality biodiesel, for an overall scum to biodiesel conversion efficiency of 65.8%.

The terms and expressions that have been employed are used as terms of description and not of limitation, and there is no intention in the use of such terms and expressions of excluding any equivalents of the features shown and described or portions thereof, but it is recognized that various modifications are possible. Thus, it should be understood that although specific embodiments are described herein with reference to optional features, modification and variation of the concepts described herein may be resorted to by those of ordinary skill in the art, and that such modifications and variations are considered to be within the scope of embodiments of the present invention.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a molding system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented, at least in part. Some examples can include a computer-readable medium or machine-readable medium encoded with instructions operable to configure an electronic device to perform methods or method steps as described in the above examples. An implementation of such methods or method steps can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The Abstract is provided to allow the reader to quickly ascertain the nature of the technical disclosure. It is submitted with the understanding that it will not be used to interpret or limit the scope or meaning of the claims.

Although the invention has been described with reference to exemplary embodiments, workers skilled in the art will recognize that changes may be made in form and detail without departing from the spirit and scope of the invention.

What is claimed is:

1. A method for production of a biodiesel comprising:
   (a) separating solids from a waste oil composition to provide a clarified waste oil composition;
   (b) acidifying the clarified waste oil composition to produce an acidified oil composition comprising free fatty acids derived from the waste oil composition;
   (c) converting at least a portion of the free fatty acids in the acidified oil composition to glycerides to provide a glyceride composition; and
   (d) reacting at least a portion of the glycerides in the glyceride composition with methanol to form fatty acid methyl esters to provide a biodiesel composition.

2. The method of claim 1, wherein acidifying the clarified oil composition comprises contacting the clarified oil composition with an aqueous acid to provide an organic fraction comprising the free fatty acids derived from the clarified oil composition and an aqueous fraction.

3. The method of claim 2, wherein the organic fraction comprises at least about 50 wt. % free fatty acids.

4. The method of claim 2, wherein the organic fraction comprises at least about 70 wt. % free fatty acids.

5. The method of claim 2, wherein acidifying the clarified oil composition further includes heating the clarified oil composition and the aqueous acid.

6. The method of claim 2, wherein acidifying the clarified oil composition comprises contacting the clarified oil composition with the aqueous acid and an organic solvent to provide the organic fraction comprising free fatty acids and the aqueous fraction.

7. The method of claim 6, further comprising separating at least a portion of the organic solvent from the organic fraction following contacting the clarified oil composition with the aqueous acid and the organic solvent to provide the acidified oil composition comprising free fatty acids derived from the waste oil.

8. The method of claim 7, wherein separating at least the portion of the organic solvent comprises heating the organic fraction to a temperature of at least 15° C., exposing the organic fraction to a pressure of about 1 atm or less, or both.

9. The method of claim 6, wherein the organic solvent is chosen from at least one of hexane, heptane, diethyl ether, ethyl acetate, and dichloromethane.

10. The method of claim 6, wherein separating at least the portion of the organic solvent further includes recycling the separated portion of the organic solvent to be used for contact with the clarified scum.

11. The method of claim 1, wherein converting at least a portion of the free fatty acids in the acidified oil composition to glycerides comprises esterification of the free fatty acids, transesterification of the free fatty acids, or both.

12. The method of claim 1, wherein converting at least a portion of the free fatty acids in the acidified oil composition to glycerides comprises contacting the free fatty acids in the acidified oil composition with glycerol.

13. The method of claim 12, wherein contacting the free fatty acids in the acidified oil composition with the glycerol is conducted at a temperature from about 175° C. to about 260° C.

14. The method of claim 1, wherein reacting at least the portion of the glycerides in the glyceride composition with the methanol to form the fatty acid methyl esters is a base-catalyzed transesterification comprising contacting at least the portion of the glycerides and the methanol in the presence of a methoxide catalyst.

15. The method of claim 14, wherein the methoxide catalyst is chosen from sodium methoxide, potassium methoxide, lithium methoxide, zinc methoxide, calcium methoxide, tributyltin methoxide, magnesium methoxide, tantalum(V) methoxide, titanium(IV) methoxide, antimony (III)methoxide, germanium methoxide, copper(II) methoxide, and combinations thereof.

16. The method of claim 1, further comprising separating glycerol and methanol from the biodiesel composition.

17. The method of claim 16, wherein separating the glycerol and the methanol from the biodiesel composition comprises (i) contacting the biodiesel composition with an acid to provide a salt of a methoxide catalyst; and
  (ii) separating the glycerol, methanol, and the salt of the methoxide catalyst from the biodiesel composition.

18. The method of claim 1, further comprising purifying the biodiesel composition with respect to the tatty acid methyl esters to produce a purified biodiesel composition.

19. The method of claim 18, wherein purifying the biodiesel composition comprises distilling the biodiesel composition.

20. The method of claim 18, further comprising the step of water washing and drying the purified biodiesel composition at a pressure of 1 atm or less.

* * * * *

UNITED STATES PATENT AND TRADEMARK OFFICE
CERTIFICATE OF CORRECTION

PATENT NO. : 9,745,530 B2
APPLICATION NO. : 15/019707
DATED : August 29, 2017
INVENTOR(S) : Ruan et al.

Page 1 of 2

It is certified that error appears in the above-identified patent and that said Letters Patent is hereby corrected as shown below:

In the Drawings

Sheet 1 of 8, Fig. 1, reference numeral 112, Line 1, delete "ACI[112" and insert --ACID 112-- therefor In the Specification In Column 1, Line 7, after "62/113,853", insert --,--

In Column 1, Line 57, after "biodiesel", insert --.--

In Column 2, Line 3, delete "orange" and insert --a range-- therefor

In Column 2, Line 31, delete ""0.000.1"" and insert --"0.000,1"-- therefor

In Column 2, Line 61, delete "oxo carbonyl)" and insert --oxo(carbonyl)-- therefor In Column 3, Line 61, delete "transesterification.)." and insert --transesterification).-- therefor In Column 4, Line 2, delete "prod" and insert --product-- therefor In Column 6, Line 27, after "of", insert --the free--

In Column 7, Line 20, delete "[5];" and insert --[5]:-- therefor

In Column 7, Line 41, delete "front" and insert --from-- therefor

In Column 8, Line 16, delete "antimony(III)methoxide," and insert --antimony(III) methoxide,-- therefor In Column 10, Line 31, after "wash", insert --222,--

Signed and Sealed this
Twenty-sixth Day of March, 2019

Andrei Iancu
*Director of the United States Patent and Trademark Office*

In Column 12, Line 55, delete "Decors" and insert --Decon-- therefor

In Column 14, Line 59, delete "Fe$_2$(SO4)$_3$," and insert --Fe$_2$(SO$_4$)$_3$,-- therefor In Column 15, Line 35, delete "-NH$^3$," and insert -- -NH$_3$,-- therefor In Column 17, Line 56, before "e.g.,", insert --(--

In Column 18, Line 49, delete "(as" and insert --as-- therefor

In Column 19, Line 60, after "layers", insert --)--

In Column 20, Line 13, delete "glycerol-ash" and insert --glycerol wash-- therefor In Column 20, Line 55, delete "6.5-5.79%." and insert --6.5-15.7%.-- therefor In Column 22, Line 49, after "microns", insert --)--

In Column 23, Line 21, after "wt/wt", insert --of--

In Column 23, Line 55, after "polarity,", insert --e.g.,--

In the Claims

In Column 30, Lines 3-4, in Claim 15, delete "antimony(III)methoxide," and insert --antimony(III) methoxide,-- therefor In Column 30, Line 15, in Claim 18, delete "tatty" and insert --fatty-- therefor